US007521533B2

(12) United States Patent
Hunt et al.

(10) Patent No.: US 7,521,533 B2
(45) Date of Patent: Apr. 21, 2009

(54) TRYPTASE POLYPEPTIDE AND USES THEREOF

(76) Inventors: John E. Hunt, 8 Bernard Avenue, Gladesville, New South Wales 2111 (AU); Hong-Wei Wang, 1 Sachem St., #1, Boston, MA (US) 02120; Hugh Patrick McNeil, 20 Tunbridge Place, Jannali, New South Wales 2226 (AU); Ahsan Husain, 8 Hilloak Court, Castle Hill, New South Wales 2154 (AU)

( * ) Notice: Subject to any disclaimer, the term of this patent is extended or adjusted under 35 U.S.C. 154(b) by 114 days.

(21) Appl. No.: 10/530,798

(22) PCT Filed: Feb. 28, 2003

(86) PCT No.: PCT/AU03/00249

§ 371 (c)(1),
(2), (4) Date: Dec. 5, 2005

(87) PCT Pub. No.: WO2004/033494

PCT Pub. Date: Apr. 22, 2004

(65) Prior Publication Data

US 2006/0177875 A1    Aug. 10, 2006

(30) Foreign Application Priority Data

Oct. 8, 2002    (AU) ............................. 2002951912

(51) Int. Cl.
*C07K 14/435*    (2006.01)
(52) U.S. Cl. .................................................... 530/350
(58) Field of Classification Search ...................... None
See application file for complete search history.

(56) References Cited

U.S. PATENT DOCUMENTS

| | | | |
|---|---|---|---|
| 5,656,660 A | 8/1997 | Lum et al. ................... 514/467 |
| 5,955,431 A | 9/1999 | Stevens et al. ................ 514/17 |
| 5,968,782 A | 10/1999 | Stevens ...................... 435/69.7 |
| 6,388,122 B1 | 5/2002 | Kido et al. .................... 560/34 |
| 2001/0053779 A1 | 12/2001 | Church et al. ............... 514/248 |
| 2002/0026654 A1 | 2/2002 | Allen et al. ................... 800/18 |
| 2002/0110895 A1 | 8/2002 | Darrow et al. .............. 435/226 |

FOREIGN PATENT DOCUMENTS

WO    WO 02/12196    2/2002

OTHER PUBLICATIONS

Entrez entry for locus Q9BZJ3 (1999).*
Attwood T., Science 2000; 290:471-473.*
Skolnick et al., Trends in Biotech. 2000; 18(1):34-39.*
Sequence alignment, 4 pages.*
Butterfield et al., "Purification of tryptase from a human mast cell line," *J Leuk Biol*, 47:409-419 (1990).
Caughey et al., Characterization of human γ-tryptases, novel members of the chromosome 16p mast cell trypase and prostasin gene families, *J Immunol*, 164:6566-6575 (2000).
Daniels et al., "Sequence, structure and pathology of the fully annotated terminal 2Mb of the short arm of human chromosome 16," *Hum Mol Genet*, 10:339-352 (2001).
Fields and Song, "A novel genetic system to detect protein-protein interactions," *Nature*, 340:245-246 (1989).
Flanagan and Leder, "The *kit* ligand: a cell surface molecule altered in steel mutant fibroblasts," *Cell*, 63:185-194 (1990).
Harris et al., ."Definition of the extended substrate specificity determinants for β-tryptases I and II," *J Biol Chem*, 276:24941-34947 (2001).
Huang et al., "Human tryptases α and β/II are functionally distinct, due in part to a single amino acid difference in one of the surface loops that forms the substrate binding cleft," *J Biol Chem*, 274:19670-19676 (1999).
Huang et al., "Formation of enzymatically active, homotypic, and heterotypic tetramer of mouse mast cell tryptases," *J Biol Chem*, 275:351-358 (2000).
McNeil et al., "Isolation, characterization, and transcription of the gene encoding mouse mast cell protease 7," *Proc Natl Acad Sci USA*, 89:11174-11178 (1992).
Min et al., "Human mouse mast cell protease 7-like tryptase genes are pseudogenes," *J Allergy Clin Immunol*, 107:315-321 (2001).
Pallaoro et al., "Characterization of genes encoding known and novel human mast cell tryptases," *J Biol Chem*, 274:3355-3362 (1999).
Park et al., "Promoted expression of mast cell-specific proteases in IgE-dependent passive cutaneous anaphylaxis responses," *Clinica Chimica Acta*, 314:231-236 (2001).
Pereira et al., "Human β-tryptase is a ring-like tetramer with active sites facing a central pore," *Nature*, 392:306-311 (1998).
Poonyachoti and Brown, "δ-opioid receptors inhibit neurogenic intestinal secretion evoked by mast cell degranulation and type I hypersensitivity," *J Neuroimmunol*, 112:89-96 (2001).
Wang et al., "δ tryptase is expressed in multiple human tissues, and a recombinant form has proteolytic activity," *J Immunol*, 169:5145-5152 (2002).
Wong et al., "Identification of a new member of the tryptase family of mouse and human mast cell proteases which possesses a novel COOH-terminal hydrophobic extension," *J Biol Chem*, 274:30784-30793 (1999).
Wong et al., "Tryptase 4, a new member of the chromosome 17 family of mouse serine proteases," *J Biol. Chem*, 276:20648-20658 (2001).
Wong et al., "Human tryptase ε (PRSS22), a new member of the chromosome 16p13.3 family of human serine proteases expressed in airway epithelial cells," *J Biol Chem*, 276:49169-49182 (2001).

(Continued)

*Primary Examiner*—Ilia Ouspenski
(74) *Attorney, Agent, or Firm*—Medlen & Carroll, LLP

(57) ABSTRACT

The present invention provides a purified expressed δ tryptase polypeptide or fragment or analogue thereof, in particular, the human δ tryptase polypeptide or fragment or analogue thereof. The present invention also provides variants of such polypeptides. The invention further relates to methods of diagnosing disease states based on expression of these polypeptides and methods of screening for compounds that interact, bind and/or modulate the activity of the polypeptides.

1 Claim, 8 Drawing Sheets

OTHER PUBLICATIONS

GenBank Accession No. AAD17845 (1998).
GenBank Accession No. AAK12909 (2000).
GenBank Accession No. AAK61272 (2000).
GenBank Accession No. NP_036349 (1999).
GenBank Accession No. Q9BZJ3 (1999).

* cited by examiner

A.

```
met leu ser leu leu leu leu ala leu pro val leu ala ser arg      -16
ATG CTG AGC CTG CTG CTG CTG GCG CTG CCC GTC CTG GCG AGC CGC       45 ala tyr ala ala pro ala pro gly gln ala leu gln gln thr gly       -1
GCC TAC GCG GCC CCT GCC CCA GGC CAG GCC CTG CAG CAA ACG GGC       90
▼
ile val gly gly gln glu ala pro arg ser lys trp pro trp gln       15
ATT GTT GGG GGG CAG GAG GCC CCC AGG AGC AAG TGG CCC TGG CAg      135 val ser leu arg val arg gly pro tyr trp met his phe cys gly       30
gtg agc ctg aga gtc cgc ggc cca tac tgg atg cac ttc tgc ggg      180 gly ser leu ile his pro gln trp val leu thr ala ala HIS cys       45
ggc tcc ctc atc cac ccc cag tgg gtg cta acc gcg gcg cac tgc      225 val glu pro asp ile lys asp leu ala ala leu arg val gln leu       60
gtg gaa ccg gac atc aag gat ctg gcc gcc ctc agg gtg caa ctg      270 arg glu gln his leu tyr tyr gln asp gln leu leu pro val ser       75
cgg gag cag cac ctc tac tac cag gac cag ctg ctg ccg gtc agc      315 arg ile ile val his pro gln phe tyr ile ile gln thr gly ala       90
agg atc atc gtg cac cca cag ttc tac atc atc cag acc ggg gcg      360

ASP ile ala leu leu glu leu glu glu pro val asn ile ser ser      105
gac atc gcc ctg ctg gag ctg gag gag ccc gtg aac atc tcc agc      405 his ile his thr val thr leu pro pro ala ser glu thr phe pro      120
cac atc cac acg gtc acg ctg ccc cct gcc tcg gag acc ttc ccc      450 pro gly met pro cys trp val thr gly trp gly asp val asp asn      135
ccg ggg atg ccg tgc tgg gtc act ggc tgg ggc gac gtg gac aat      495 asn val his leu pro pro pro tyr pro leu lys glu val glu val      150
aat gtg cac ctg ccg ccg cca tac ccg ctg aag gag gtg gaa gtc      540 pro val val glu asn his leu cys asn ala glu tyr his thr gly      165
ccc gta gtg gaa aac cac ctt tgc aac gcg gaa tat cac acc ggc      585 leu his thr gly his ser phe gln ile val arg asp asp met leu      180
ctc cat acg ggc cac agc ttt caa atc gtc cgc gat gac atg ctg      630 cys ala gly ser glu asn his asp ser cys gln gly asp SER gly      195
tgt gcg ggg agc gaa aat cac gac tcc tgc cag ggt gac tct gga      675 gly pro leu val cys lys val asn gly thr ***                      205
ggg ccc ctg gtc tgc aag gtg aat ggc acc taa ctg cag gcg ggc      720 gtg gtc agc tgg gag gag agc tgt gcc cag ccc aac cgg cct ggc      765 atc tac acc cgt gtc acc tac tac ttg gaC TGG ATC CAC CAC TAT      810
```

```
                                      ▼
αI    MLSLLLLALPVLASRAYAAPAPVQALQQAGIVGGQEAPRSKWPWQVS LRV      20
αII   --------------P------------------------------- --- 
βI    --N-----------------G----RV------------------- ---
βII   --N-----------------G----RV------------------- ---
βIII  --N-----------------G----RV------------------- ---
δI    -----------P--V---G-----T--------------------- ---
δII   -----------P--V---G-----T--------------------- ---

αI    RDRYWMHF GGSLIHPQWVLTA AHCLGP DVKDLATLRVQLREQHLYYQDQ    70
αII   -------- ------------- ------ --------------------
βI    HGP----- ------------- --V--- -----A-------------
βII   HGP----- ------------- --V--- -----A-------------
βIII  -------- ------------- --V--- -----A-------------
δI    -GP----- ------------- --ME-- -I---A-------------
δII   -GP----- ------------- --VE-- -I---A-------------
           A                    B

αI    LLPVSRIIVHPQFY IIQTGAD IALLELEEPVNISSRVHTVML PPAS ETFP  120
αII   -------------- -------- ------------------- ---- ----
βI    -------------- TA-I--- -----------V--H----T ---- ----
βII   -------------- TA-I--- ---------KV--H----T- ---- ----
βIII  -------------- TA-I--- ------------------T- ---- ----
δI    -------------- ------- -------------HI---T- ---- ----
δII   -------------- ------- -------------HI---T- ---- ----
                       C                            D

αI    PGMPCWVTGWGDVDNDEPLPPPFPLKQVKVPIMENHICDAKY HLGAYTGD     170
αII   ----------------------------------------- ---------
βI    -----------------R----------------------- ---------
βII   -----------------R----------------------- ---------
βIII  -----------------R----------------------- ---------
δI    --------------NVH----Y---E-E--VV---L-N-E- -T-LH--H
δII   --------------NVH----Y---E-E--VV---L-N-E- -T-LH--H
                                                     3

αI    DV RIIRDDMLCAGNSQR DSCKGDSG GPLVCKVNGTWLQAG VVSWDEGC AQ  220
αII   -- --------------TR- -Q---- ---------------- -------- --
βI    -- -V-----------TR- -Q---- ---------------- ----G--- --
βII   -- -V-----------TR- -Q---- ---------------- ----G--- --
βIII  -- -V-----------TR- -Q---- ---------------- ----G--- --
δI    SFQ-V-------SENH --------- ---------X
δII   SFQ-V-------SENH --------- ---------X
                          1                          2

αI    PNRPGIYTRVTYYLDWIHHYVPKKP                  245
αII   -------------------------
βI    -------------------------
βII   -------------------------
βIII  -------------------------
```

Fig. 3

&& # TRYPTASE POLYPEPTIDE AND USES THEREOF

This application is a U.S. national entry of International Application No. PCT/AU2003/000249, filed on Feb. 28, 2003, which claims priority from Australian Patent Application No. 2002951912, filed on Oct. 8, 2002.

TECHNICAL FIELD

The present invention relates to the expressed delta (δ) tryptase polypeptide, in particular the human δ tryptase protein. The present invention also relates to uses of this polypeptide, in particular for diagnosing disease states and screening for δ tryptase modulator and inhibitor compounds.

BACKGROUND OF THE INVENTION

Mast cells are highly granulated, tissue-resident, effector cells of the immune system. They may be activated via their high affinity IgE receptors or by a number of alternate mechanisms. Following activation they secrete a variety of preformed mediators including histamine, proteoglycans, and a range of serine proteases that are active at neutral pH. Two major families of these proteases have been identified: chymases and tryptases, and they represent the major protein component of the mast cell.

A role has been proposed for mast cell tryptases in the development of a number of inflammatory diseases, including diseases of the respiratory tract, such as asthma and allergic rhinitis, rheumatoid arthritis, and inflammatory bowel disease. Despite the underlying causes of these diseases not being fully understood, it is known that the number of mast cells is increased in the airways of patients with asthma, and in the synovial tissue of patients with rheumatoid arthritis.

Accordingly, there is a clear need to elucidate the role of mast cells in inflammatory disease phenotypes and to develop suitable agents for the prevention and/or inhibition of mast cell-mediated inflammation.

There is a wealth of evidence indicating that many mast cell products are pro-inflammatory. However, recent reports suggest that tryptase may be one of the most important in the development of asthma and inflammatory bowel disorders. Tryptases have been shown to inactivate vasoactive intestinal peptide (VIP), one of only two naturally occurring bronchodilators expressed in the airway, and to induce smooth muscle cell mitosis and hyper-reactivity. More importantly tryptase inhibitors inhibit allergen-induced airway hyperreactivity and markers of inflammation. Tryptase also induces IL-8 secretion from airway epithelial cells, so promoting airway inflammation.

Tryptases have thus become the focus of considerable attention, and there exists a need for the elucidation of effective modulators and inhibitors of tryptases which may be used in treating or preventing mast cell-mediated inflammatory diseases.

A major impediment to determining the role of tryptases, and therefore to developing effective modulators, inhibitors and treatments, has been the confusion over how many different functional human tryptases are expressed. A number of tryptase genes are known to be grouped on chromosome 16, mapping to 16p13.3. These include the gene encoding βI tryptase and its allelic partner αII tryptase, the allelic genes encoding βII and βIII tryptase, two allelic variants of a transmembrane tryptase called gamma (γ) tryptase, and two allelic variants of another tryptase originally named "mMCP-7-like" (Pallaoro et al., 1999; Caughey et al., 2000). Of these, cDNAs have been cloned for all loci except for that encoding "mMCP-7-like" tryptase. Recently the cloning of a more distantly related member, epsilon (ε) tryptase, which is approximately 40% similar to the α/β tryptases has also been described (Wong et al., 2001).

The mMCP-7-like tryptase was so named due to homology between its fifth exon and the murine tryptase mouse mast cell protease (mMCP)-7 (Pallaoro et al., 1999; McNeil et al., 1992). Recently it has been reported (Min et al., 2001) that the mMCP-7-like gene is not transcribed. Based on the examination of a number of human tissues and cell lines for transcription of the mMCP-7-like gene, Min et al. reported that mRNA is absent and concluded that the mMCP-7-like gene is a pseudogene. However the present inventors have surprisingly discovered that the human mMCP-7-like tryptase is indeed expressed and have named the gene, and its polypeptide product delta (δ) tryptase.

SUMMARY OF THE INVENTION

According to a first embodiment of the present invention there is provided a purified, expressed δ tryptase polypeptide or fragment or analogue thereof. Preferably, the expressed δ tryptase polypeptide is the human δ tryptase protein. More preferably, the expressed human δ tryptase protein has the amino acid sequence as set forth in SEQ ID NO:1 or SEQ ID NO:2, or the amino acid sequence as set forth in SEQ ID NO:1 or SEQ ID NO:2 including one or more conservative amino acid substitutions.

According to a second embodiment of the present invention there is provided a purified, expressed variant of the δ tryptase polypeptide of the first embodiment, or a fragment or analogue of this variant. Preferably, the variant δ tryptase polypeptide is the product of alternative splicing of the primary RNA transcript. More preferably the variant polypeptide has the amino acid sequence as set forth in SEQ ID NO:3.

In a third embodiment the present invention provides a recombinant host cell expressing the polypeptide or fragment or analogue thereof of the first or second embodiment.

In a fourth embodiment the present invention provides an antibody that selectively binds to the polypeptide or fragment or analogue thereof of the first or second embodiment.

In a fifth embodiment the present invention provides a method of identifying a compound that interacts with the polypeptide or fragment or analogue thereof of the first or second embodiment, the method comprising the steps of:

(a) contacting a candidate compound with the polypeptide or fragment or analogue thereof of the first or second embodiment under conditions suitable to enable interaction of the candidate compound to the polypeptide or fragment or analogue thereof; and (b) assaying for activity of the polypeptide or fragment or analogue thereof.

Preferably, assaying for activity of the polypeptide or fragment or analogue thereof comprises adding a labelled substrate and measuring a change in the labelled substrate.

According to a sixth embodiment of the present invention there is provided a method of identifying a compound that binds to the polypeptide or fragment or analogue thereof of the first or second embodiment, the method comprising the steps of:

(a) contacting a candidate compound with the polypeptide or fragment or analogue thereof of the first or second embodiment; and (b) assaying for the formation of a complex between the candidate compound and the polypeptide or fragment or analogue thereof.

Preferably the assay for the formation of a complex is a competitive binding assay or a two-hybrid assay.

According to a seventh embodiment of the present invention there is provided a method of screening for a compound that modulates the activity of the polypeptide or fragment or analogue thereof of the first or second embodiment, the method comprising the steps of:

(a) contacting the polypeptide or fragment or analogue thereof of the first or second embodiment with a candidate compound under conditions suitable to enable interaction of the candidate compound to the polypeptide; and (b) assaying for activity of the polypeptide of the first or second embodiment.

Preferably, assaying for activity of the polypeptide comprises adding a labelled substrate and measuring a change in the labelled substrate.

Preferably the modulation of activity is an inhibition of activity of the polypeptide or fragment or analogue thereof of the first or second embodiment.

According to an eighth embodiment of the present invention there is provided a method of diagnosing a disease state, or predisposition to a disease state, in a subject, the method comprising the steps of:

(a) isolating a biological sample from the subject; and (b) assaying for expression of the polypeptide or fragment or analogue thereof of the first or second embodiment in the sample.

Preferably, assaying for the expression of the polypeptide or fragment or analogue thereof comprises contacting the biological sample with a compound capable of interacting with the polypeptide such that the interaction can be detected.

Preferably the compound capable of interacting with the polypeptide or fragment or analogue thereof is an anti-δ tryptase antibody.

Preferably the disease state is an inflammatory disease. More preferably, the disease is a mast-cell associated inflammatory disease. Most preferably the inflammatory disease is selected from the group consisting of: asthma, allergic rhinitis, urticaria, angioedema, eczematous anaphylaxis, dermatitis such as atopic dermatitis, hyperproliferative skin disease, peptic ulcers, inflammatory bowel disorder, ocular and vernal conjunctivitis, rheumatoid arthritis, and inflammatory skin conditions.

According to a ninth embodiment of the present invention there is provided a method of identifying an agent which is an inhibitor of mast cell-mediated inflammation, the method comprising contacting a cell or cell extract with the agent, determining whether there is a change in the activity of a δ tryptase polypeptide or fragment or analogue thereof, and thereby determining whether the agent is an inhibitor of mast cell-mediated inflammation.

According to a tenth embodiment of the present invention there is provided a method of identifying an agent suitable for use in the treatment or prevention of a mast cell-mediated inflammatory disease state in a subject, the method comprising isolating a biological sample from the subject, contacting the sample with a candidate agent, determining whether there is a change in the activity a δ tryptase polypeptide or fragment or analogue thereof in the sample, and thereby determining whether the agent is suitable for use in the treatment of the disease state.

Preferably the inflammatory disease is selected from the group consisting of: asthma, allergic rhinitis, urticaria, angioedema, eczematous anaphylaxis, dermatitis such as atopic dermatitis, hyperproliferative skin disease, peptic ulcers, inflammatory bowel disorder, ocular and vernal conjunctivitis, rheumatoid arthritis, and inflammatory skin conditions.

In an eleventh embodiment the present invention provides compounds identified by the methods of the fifth, sixth, seventh, ninth and tenth embodiments.

In a twelfth embodiment the present invention provides a method for treating or preventing a disease state in a subject, the method comprising administering to the subject a therapeutically effective amount of a compound identified by the method of any one of the fifth, sixth, seventh, ninth and tenth embodiments.

According to a thirteenth embodiment of the present invention there is provided a kit comprising the polypeptide or fragment or analogue thereof of the first or second embodiment. Alternatively, or in addition, the kit may contain an antibody of the fourth embodiment. Preferably the kit is used for carrying out the methods of the fifth, to the tenth embodiments.

BRIEF DESCRIPTION OF THE DRAWINGS

Preferred embodiments of the present invention will now be described, by way of example only, with reference to the accompanying drawings.

FIG. 3. Amino acid sequences of δI tryptase (SEQ ID NO:2) and δII tryptase (SEQ ID NO:1) compared to that of tryptases αI (SEQ ID NO:22), αII (SEQ ID NO:23),βI (SEQ ID NO:24), βII (SEQ ID NO:25), and βIII (SEQ ID NO:26). A dash (—) indicates the presence of an identical amino acid. Numbering begins at the first residue of the mature enzyme, which is indicated by an arrow (▼). The seven loops comprising the substrate binding cleft are boxed and labelled A, B, C, D, 1, 2, and 3. The H, D and S of the catalytic triad are marked with a hash (#). The premature termination codons of the δ tryptases are marked with an X. The peptide sequence used as the immunogen for anti δ tryptase is underlined ( ... ).

DEFINITIONS

Figure 1:
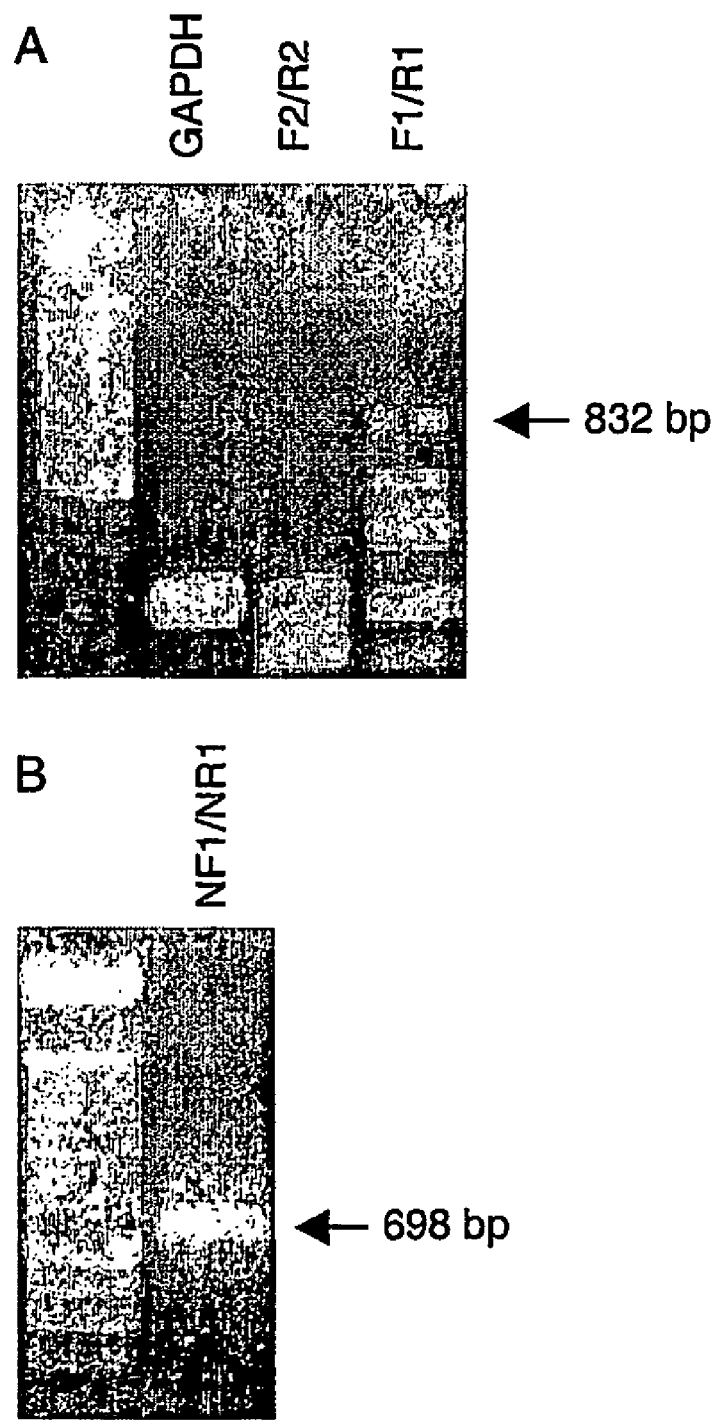
FIG. 1. RT-PCR amplification of the transcript for δ tryptase. A). RT-PCR of total RNA isolated from the HMC-1 cell line using two primer pair combinations, F1/R1 and F2/R2. GAPDH was amplified as a control. The correct sized band (832 bp) for δ tryptase was only generated using the F1/R1 primer pair. B). PCR amplification using the purified 832 bp band from FIG. 1A as the DNA template, and the nested primer set NF1/NR1 to generate the expected 698 bp product.

As used herein the term "polypeptide" means a polymer made up of amino acids linked together by peptide bonds.

The term "purified" means that the material in question has been removed from its host, and associated impurities reduced or eliminated. Essentially, it means an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "fragment" refers to a polypeptide molecule that is a constituent of the full-length δ tryptase polypeptide and possesses qualitative biological activity in common with the full-length δ tryptase polypeptide. The fragment may be derived from the full-length δ tryptase polypeptide or alternatively may be synthesised by some other means, for example chemical synthesis.

The term "analogue" as used herein with reference to a polypeptide means a polypeptide which is a derivative of the polypeptide of the invention, which derivative comprises addition, deletion, substitution of one or more amino acids, such that the polypeptide retains substantially the same function as the δ tryptase polypeptide identified above.

The term "variant" as used herein refers to a polypeptide which is produced from the nucleic acid encoding δ tryptase, but differs from the wild type δ tryptase in that it is processed differently such that it has an altered amino acid sequence. For example a variant may be produced by an alternative splicing pattern of the primary RNA transcript to that which produces wild type δ tryptase.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

The term "modulator" as used herein refers to any compound capable of interacting with a δ tryptase polypeptide, or fragment, analogue or variant thereof, so as to alter the expression, catalytic activity, or other function of the δ tryptase polypeptide, or fragment, analogue or variant thereof. A modulator may be, for example, an agonist, antagonist or inhibitor of the δ tryptase polypeptide, or fragment, analogue or variant thereof. Modulators may include antibodies, low molecular weight peptides, nucleic acids or non-proteinaceous organic molecules, for example.

As used herein the term "treatment", refers to any and all uses which remedy a disease state or symptoms, prevent the establishment of disease, or otherwise prevent, hinder, retard, or reverse the progression of disease or other undesirable symptoms in any way whatsoever.

As used herein the term "therapeutically effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

In the context of this specification, the term "comprising" means "including principally, but not necessarily solely". Furthermore, variations of the word "comprising", such as "comprise" and "comprises", have correspondingly varied meanings.

BEST MODE OF PERFORMING THE INVENTION

The present invention is based on the inventors' surprising finding that the human δ tryptase protein is not a pseudogene, but rather is expressed in a number of human tissues.

The inventors have also generated an antibody directed against the human δ tryptase protein and a recombinant δ tryptase protein, displaying proteolytic activity, in a bacterial expression system. The recombinant δ tryptase generated possesses full catalytic activity.

δ Tryptase Polypeptides

Accordingly, an embodiment of the present invention provides the isolated, expressed δ tryptase polypeptide, or fragment or analogue thereof. Particularly, the δ tryptase polypeptide of the present invention is the human δ tryptase protein, having the amino acid sequence set forth in SEQ ID:1 (δI) or SEQ ID:2 (δII). It will be appreciated that this amino acid sequence may include one or more conservative amino acid substitutions such that although the primary sequence of the polypeptide is altered, the activity of the polypeptide is retained. The present invention also relates to variants of the δ tryptase polypeptide. In a preferred embodiment, the variant δ tryptase polypeptide is a polypeptide having the amino acid sequence as set forth in SEQ ID NO:3. The variant polypeptide sequence depicted in SEQ ID NO:3 is generated by alternative splicing of the primary δ tryptase transcript, such that the initial 27 nucleotides of exon 4 are excised, resulting in a polypeptide 9 amino acids shorter than the mature full length human δ tryptase.

The in vivo expression of human δ tryptase transcript has been observed in a wide variety of tissues, including lung, heart, stomach, spleen, skin, and colon. The δ tryptase transcript appears to be most abundant in the lung and colon but is also expressed in the heart and stomach. The present application provides the first evidence that the human δ tryptase gene is expressed at the transcriptional level.

The human δ tryptase polypeptide of the present invention is expressed in a number of tissues including colon, lung, heart and synovial tissue. In the colon, the vast majority of δ tryptase-positive cells were found to be in the mucosal compartment, with only one or two individual δ tryptase-positive cells located in the submucosa or muscle layers. This suggests that δ tryptase may be useful as marker of a new mast cell phenotype that is more common in the mucosa.

Detection of the δ tryptase transcript in the HMC-1 cell line indicates that its expression may be primarily restricted to mast cells. However immunohistochemistry results suggest that δ tryptase may be expressed by other cells in addition to mast cells and/or that discordant mast cell phenotypes may exist characterised by discordant expression of δ tryptase and the α/β tryptases.

The mature human δ tryptase enzyme is 40 amino acids shorter than the well described α/β family of human tryptases. However the catalytic triad, essential for proteolytic activity, remains intact. The substrate binding cleft of tryptases comprises seven major loops in the polypeptide chain, named A, B, C, D, 3, 1 and 2 in order from the N terminus (see FIG. 3). The loss of the terminal 40 amino acids in δ tryptase means that loop 2 (residues 211-218 in the α/β tryptases) is not present in δ tryptase. This loop forms part of the S1, S2 and S3 sites of the enzyme and even single amino acid changes within this loop is known to alter the substrate specificity of tryptases (Huang et al. 1999). Consistent with this, a recombinant form of δ tryptase, expressed in bacterial cells, has been shown to differ from βII tryptase in its ability to cleave a panel of three substrates. It appears that the substrate specificity of δ tryptase is likely to be quite different from that of previously characterised tryptases.

Huang et al. (2000) have reported that two mouse tryptases, mMCP-6 and mMCP-7 could form enzymatically-active heterotypic tetramers. Further, Harris et al. (2001) have suggested that residues on neighbouring tryptase monomers acted together within the tetramer framework to form parts of the extended substrate recognition site. Taken together these results suggest that even if its proteolytic efficiency is low, δ tryptase may modulate the activity of other tryptases by forming heterotypic tetramers.

In vitro detection of the polypeptides or fragments or analogues thereof of the present invention may be achieved using a variety of techniques including ELISA (enzyme linked immunosorbent assay), Western blotting, immunoprecipitation and immunofluorescence. Such techniques are commonly used by those of skill in the art. Similarly, suitable techniques of the in vivo detection of the polypeptide, or fragments or analogues thereof, including immunohistochemistry using a labelled anti-δ tryptase antibody, will be readily understood by persons skilled in the art.

In accordance with the present invention, fusion proteins may also be engineered to improve characteristics of the δ tryptase polypeptides, or fragments or analogues thereof, of the present invention. For example, a region of additional amino acids, particularly charged amino acids, may be added to the N-terminus of the δ tryptase polypeptides to improve stability during purification from a host cell. Alternatively, peptide moieties may be added to the polypeptide to facilitate purification. Such regions may be removed prior to final preparation of the polypeptide. The addition of peptide moieties to facilitate handling of polypeptides are routine techniques well known to those of skill in the art.

Uses of the δ Tryptase Polypeptides

Antibodies

The present invention provides antibodies that selectively bind to the δ tryptase of the present invention, as well as fragments and analogues thereof. Suitable antibodies include, but are not limited to polyclonal, monoclonal, chimeric, humanised, single chain, Fab fragments, and an Fab expression library. Antibodies of the present invention may act as agonists or antagonists of δ tryptase polypeptides, or fragments or analogues thereof.

Preferably antibodies are prepared from discrete regions or fragments of the tryptase polypeptide, in particular those involved in conferring protease activity and/or partner or substrate binding. An antigenic δ tryptase polypeptide contains at least about 5, and preferably at least about 10, amino acids.

Methods for the generation of suitable antibodies will be readily appreciated by those skilled in the art. For example, an anti-δ tryptase monoclonal antibody, typically containing Fab portions, may be prepared using the hybridoma technology described in Antibodies-A Laboratory Manual, Harlow and Lane, eds., Cold Spring Harbor Laboratory, N.Y. (1988).

In essence, in the preparation of monoclonal antibodies directed toward δ tryptase polypeptide, fragment or analogue, thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et al., Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies to δ tryptase, or fragments or analogues thereof. For the production of δ tryptase polyclonal antibody, various host animals can be immunized by injection with the δ tryptase polypeptide, or a fragment or analogue thereof, including but not limited to rabbits, mice, rats, sheep, goats, etc. Further, the δ tryptase polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

Screening for the desired δ tryptase antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti δ tryptase antibody. Alternatively, the anti δ tryptase antibody may be detected by virtue of its binding with a secondary antibody or reagent which is appropriately labelled. A variety of methods are known in the art for detecting binding in an immunoassay and are within the scope of the present invention.

Antibodies of the present invention can be used in diagnostic methods and kits that are well known to those of ordinary skill in the art to detect qualitatively or quantify δ tryptase in a body fluid or tissue, and results from these tests can be used to diagnose or determine predisposition to an inflammatory disease in a subject.

The antibody (or fragment thereof) raised against δ tryptase or a fragment or analogue thereof has binding affinity for δ tryptase. Preferably, the antibody (or fragment thereof) has binding affinity or avidity greater than about $10^5$ $M^{-1}$, more preferably greater than about $10^6$ $M^{-1}$, more preferably still greater than about $10^7$ $M^{-1}$ and most preferably greater than about $10^8$ $M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Modulator and Inhibitor Compounds

In addition to specific anti-δ tryptase antibodies, the polypeptide of the present invention, and fragments and analogues thereof are particularly useful for the screening and identification of compounds and agents that interact with δ tryptase. In particular, desirable compounds are those that modulate the activity of δ tryptase. Such compounds may modulate by activating, increasing, inhibiting or preventing δ tryptase activity. Suitable compounds may exert their effect on δ tryptase by virtue of either a direct (for example binding) or indirect interaction.

Compounds which bind, or otherwise interact with δ tryptase, and specifically compounds which modulate the activity of δ tryptase, may be identified by a variety of suitable methods. Interaction and/or binding may be determined using standard competitive binding assays or two-hybrid assay systems.

For example, the two-hybrid assay is a yeast-based genetic assay system (Fields and Song, 1989) typically used for detecting protein-protein interactions. Briefly, this assay takes advantage of the multi-domain nature of transcriptional activators. For example, the DNA-binding domain of a known transcriptional activator may be fused to a δ-tryptase protein, or fragment or analogue thereof, and the activation domain of the transcriptional activator fused to a candidate protein. Interaction between the candidate protein and the δ-tryptase, or fragment or analogue thereof, will bring the DNA-binding and activation domains of the transcriptional activator into close proximity. Interaction can thus be detected by virtue of transcription of a specific reporter gene activated by the transcriptional activator.

Alternatively, affinity chromatography may be used to identify δ tryptase binding partners. For example, a δ tryptase polypeptide, or fragment or analogue thereof, may be immobilised on a support (such as sepharose) and cell lysates passed over the column. Proteins binding to the immobilised δ tryptase polypeptide, fragment or analogue can then be eluted from the column and identified. Initially such proteins may be identified by N-terminal amino acid sequencing for example.

Alternatively, in a modification of the above technique, a fusion protein may be generated by fusing a δ tryptase polypeptide, fragment or analogue to a detectable tag, such as alkaline phosphatase, and using a modified form of immunoprecipitation as described by Flanagan and Leder (1990).

Methods for detecting compounds that modulate δ tryptase activity may involve combining δ tryptase with a candidate compound and a suitable labelled substrate and monitoring the effect of the compound on δ tryptase by changes in the substrate (may be determined as a function of time). Suitable labelled substrates include those labelled for colourimetric, radiometric, fluorimetric or fluorescent resonance energy transfer (FRET) based methods, for example. Alternatively, compounds that modulate the activity of δ tryptase may be identified by comparing the catalytic activity of δ tryptase in the presence of a candidate compound with the catalytic activity of δ tryptase in the absence of the candidate compound.

The present invention also contemplates compounds which may exert their modulatory effect on δ tryptase by altering expression of the protein. In this case, such compounds may be identified by comparing the level of expression of δ tryptase in the presence of a candidate compound with the level of expression of δ tryptase in the absence of the candidate compound.

δ tryptase polypeptides and appropriate fragments and analogues can be used in high-throughput screens to assay candidate compounds for the ability to bind to, or otherwise interact with δ tryptase. These candidate compounds can be further screened against functional δ tryptase to determine the effect of the compound on δ tryptase activity.

It will be appreciated that the above described methods are merely examples of the types of methods which may be employed to idenfity compounds that are capable of interacting with, or modulating the activity of, the δ tryptase polypeptides, and fragments and analogues thereof, of the present invention. Other suitable methods will be known to persons skilled in the art and are within the scope of the present invention.

By the above methods, compounds can be identified which either activate (agonists) or inhibit (antagonists) δ tryptase activity. Such compounds may be, for example, antibodies, low molecular weight peptides, nucleic acids or non-proteinaceous organic molecules.

Potential modulators of δ tryptase activity, for screening by the above methods, may be generated by a number of techniques known to those skilled in the art. For example, various forms of combinatorial chemistry may be used to generate putative non-peptide modulators. Additionally, techniques such as nuclear magnetic resonance (NMR) and X ray crystallography, may be used to model the structure of δ tryptase polypeptides, fragments and analogues and computer predictions used to generate possible modulators (in particular inhibitors) that will fit the shape of the substrate binding cleft of the tryptase.

Disease Treatment and Diagnosis

Compounds identified by the above methods may be useful as therapeutic agents. These compounds find use, for example, in treating or preventing a disease state in a subject, by administering a therapeutically effective amount of such a compound to the subject. Accordingly, pharmaceutically useful compositions comprising modulators of δ-tryptase activity for use in treating or preventing disease states associated with tryptase activity are contemplated. Suitable compositions may be formulated according to known methods such as, for example, by the admixture of a pharmaceutically acceptable carrier and an effective amount of the modulator.

The δ tryptase polypeptide of the present invention, fragments and analogues thereof, and anti δ tryptase antibodies are also particularly useful for determining the presence of a disease state in a subject, or the predisposition of a subject to a disease state, the disease state being one that is associated with tryptase activity and/or mast cell activation. The δ tryptase polypeptide of the present invention, and fragments and analogues thereof, can be used to identify compounds that modulate catalytic activity of the δ tryptase polypeptide either in its natural state or in an altered form that causes a specific disease or pathology.

Accordingly, the present invention provides suitable methods for determining the expression of δ tryptase transcript in biological samples (including cells and tissues), such as reverse transcription polymerase chain reaction (RT-PCR) and real time quantitative (RTQ) RT-PCR. The invention also provides methods for detecting the expression of δ tryptase polypeptide (as described above).

Diseases which the polypeptides and methods of the present invention are particularly useful for diagnosing (presence or predisposition in a subject) are inflammatory diseases and disorders associated with hypersensitivity reactions. In particular, diseases characterised by mast cell-mediated inflammation are contemplated. These include inflammatory disorders of the respiratory tract, inflammatory skin conditions and other inflammatory disorders.

In particular, suitable diseases and disorders include asthma, allergic rhinitis, urticaria and angioedema, eczematous anaphylaxis, dermatitis such as atopic dermatitis, hyperproliferative skin disease, peptic ulcers, inflammatory bowel disorder, ocular and vernal conjunctivitis, rheumatoid arthritis, and inflammatory skin conditions.

Modulator and inhibitor compounds and agents of the present invention may be administered as compositions either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg is to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m², and still even more preferably about 75 to about 150 mg/m².

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Kits

In accordance with the present invention, kits containing δ-tryptase polypeptide, fragment(s) or analogue(s) thereof, or anti-δ tryptase antibodies may be prepared. Such kits may is be used, for example, to detect the presence of δ-tryptase, or fragments or analogues thereof, in a biological sample. Detection using such kits is useful for a variety of purposes, including but not limited to disease diagnosis, epidemiological studies and performing screening methods of the present invention.

Kits of the present invention comprising one or more anti δ tryptase antibodies may further comprise one or more control antibodies which do not react with the δ tryptase polypeptides, or fragments or analogues thereof, of the present invention. Additionally, kits may contain means for detecting the binding of an anti δ tryptase antibody to a δ tryptase polypeptides, or fragments or analogues thereof, of the present invention. For example the one or more anti δ tryptase antibodies may be conjugated to a detectable substrate such as a fluorescent, radioactive or luminescent compound, an enzymatic substrate, or to a second antibody which recognizes the anti δ tryptase antibody and is conjugated to a detectable substrate.

Kits according to the present invention may also include other components required to conduct the methods of the present invention, such as buffers and/or diluents. The kits typically include containers for housing the various components and instructions for using the kit components in the methods of the present invention.

The present invention will now be described with reference to specific examples, which should not be construed as in any way limiting the scope of the invention.

EXAMPLES

Example 1

Cloning of δ Tryptase cDNA

Sources of RNA.

HMC-1 cells ($5 \times 10^6$, a kind gift from Dr J H Butterfield) were lysed in 1 ml of TRI REAGENT™ (Sigma-Aldrich, Sydney, Australia), and 0.2 ml of chloroform added. Following centrifugation, the aqueous phase was transferred to a fresh tube and 0.5 ml of isopropanol added. The RNA pellet was collected by centrifugation, washed with 75% ethanol, dissolved in $dH_2O$ and stored at −80° C. until required.

Total RNA from adult lung, heart, stomach, spleen, skin, colon, fetal heart and fetal lung, and poly($A^+$) RNA isolated from human lung, were obtained from commercial sources (Invitrogen, Carlsbad, Calif.).

Preparation of cDNA.

First strand cDNAs were generated using the cDNA Cycle® kit (Invitrogen) from total RNA isolated from the HMC-1 cell line and from poly($A^+$) RNA isolated from human lung. 1.5 µg of HMC-1 total RNA (or 300 ng of lung poly $A^+$ mRNA) and 1 µl of oligo (dT) primer were heated at 65° C. for 10 min to remove secondary structure. Reverse transcription was performed for 1 h at 42° C. in a solution containing 1 µl of RNase inhibitor, 4 µl of 5×RT buffer, 1 µl of 100 mM dNTPs, 1 µl of 80 mM sodium pyrophosphate and 0.5 µl AMV reverse transcriptase. The reaction was terminated by incubating the mixture at 95° C. for 2 min, and was then placed on ice immediately.

PCR Amplification and Cloning of cDNAs.

PCR amplification of first strand cDNA was performed within 2h of the reverse transcription reaction. Initially a nested PCR approach was used to amplify cDNAs, using primers designed according to the sequence of a gene that we isolated independently and named delta (δ) tryptase (data not shown), and according to the published sequence of the mMCP-7-like genes (GenBank accession numbers AF099147 and AF098327) (Pallaoro et al., 1999). Two sets of primers (F1=5'-CCC GTC CTG GCG AGC CCG-3' (SEQ ID NO:4)/R1=5'-CAG TGA CCC AGG TGG ACA C-3' (SEQ ID NO:5) and F2=5'-AGT GGC CAG GAT GCT GAG C-3' (SEQ ID NO:6)/R2=5'-TTT GGA CAG GAG GGG CTG GCT-3' (SEQ ID NO:7) were employed to amplify the initial product, and a single nested primer pair (NF1=5'-GAG CAA GTG GCC CTG GCA-3' (SEQ ID NO:8)/NR1=5'-GGA CAT AGT GGT GGA TCC AG-3' (SEQ ID NO:9), see FIG. 2A) was used on the resulting template. In later experiments a single primer pair (F3=5'-TGC AGC AAA CGG GCA TTG TTG-3' (SEQ ID NO:10), and R3=5'-AAA GCT GTG GCC CGT ATG GAG-3' (SEQ ID NO:11) was used to amplify δ tryptase cDNAs.

The PCR reactions were carried out with 2.5 units of AmpliTaq Gold™ (Perkin Elmer, Branchburg, N.J.) and 2 μl of the reverse transcriptase reaction mixture. The total reaction volume was 50 μl with a final concentration of 10 mM Tris/HCl, pH 8.3, 50 mM KCl, 2 mM $MgCl_2$, 0.2 mM dNTPs, and 0.1 μM of the appropriate 5' and 3' primers. After an initial incubation for 5 min at 94° C., samples were subjected to 35 cycles of PCR (45 s at 95° C., 60 s at 55° C., and 60 s at 72° C.). This was followed by a final extension step of 72° C. for 10 min. PCR products (10 μl) were visualized on a 1% agarose gel. Appropriately-sized products were excised from the gel, purified with QIAquick gel extraction kit (QIAGEN, Chatsworth, Calif.) and ligated into the plasmid vector pCR®2.1-TOPO (Invitrogen). The ligation mixture was then used to transform TOP10 cells (Invitrogen). The transformation mixture was plated onto LB/agar plates containing Ampicillin (50 μg/ml), and coated with X-gal to enable blue/white color selection. Plasmids containing the appropriate sized inserts were screened for the presence of tryptase cDNAs by PCR using the primer set NF1/NR1. Plasmid DNA was then purified from clones identified in this manner using a commercial kit (Qiagen). Nucleotide sequencing was performed either in-house using an ABI Prism® BigDye Terminator Cycle Sequencing Ready Reaction Kit and an ABI377 PRISM DNA Sequencer (PE Applied Biosystems, Foster City, Calif.), or at a core facility (SUPAMAC, Sydney, Australia).

δ Tryptase cDNA Sequences

Figure 2B:
FIG. 2. A). The cDNA (SEQ ID NO:20) and putative amino acid (SEQ ID NO:1) sequences of δII tryptase. The δII cDNA sequence matched the putative exon sequence of the mMCP-7-like II gene. The δI cDNA (not shown in FIG. 2) matched the exonic sequence of the partial mMCP-7-like I gene. Consistent with the published gene sequences, there were two nucleotide differences between the two cDNA sequences; $G^{216}$ (δII cDNA) to A (δI cDNA) (nucleotide numbering starts from the translation initiation codon), and $G^{226}$ (δII cDNA) to A (δI cDNA). Only the second of these differences results in an amino substitution (Val in δII to Met in δI). Actual nucleotide sequence of cloned RT-PCR product is shown in bold lower case lettering. The location of the forward (NF1) and reverse (NR1) primers are indicated by arrows. The first amino acid of the mature enzyme is italicized and in bold. The three members of the catalytic triad, His, Asp and Ser, are in capitals and underlined. Nucleotide numbering begins from the translation initiation codon (Met). Amino acid numbering begins from the first residue of the mature enzyme (Ile). The position of the forward (●→) and reverse (←♦) primers, and the Taqman probe (═══) for RTQ-RTPCR are indicated. B). The amino acid sequence of a portion of a variant δ tryptase polypeptide (SEQ ID NO:21). This variant is the product of alternative splicing which results in the excision of 27 nucleotides from the beginning of exon 4, and thus the deletion of 9 amino acids from the polypeptide when compared to the full length δ tryptase polypeptide. The location of the 9 amino acids present in the full length polypeptide but missing in the variant polypeptide is indicated by a vertical arrow (⇓).

PCR amplification of the first strand cDNA template from the HMC-1 cell line generated multiple bands, but only reactions using the F1/R1 primer pair resulted in amplification of the expected 832 bp product (FIG. 1A). The correctly sized band was excised and used as a PCR template with the nested primer pair NF1/NR2. The expected 698 bp PCR product was generated (FIG. 1B), excised, and cloned into the pCR2.1 vector. Sequencing of ten clones revealed the presence of two distinct cDNAs that we have named δI tryptase and δII tryptase (GenBank accession numbers AY055427 and AF206664 respectively). The δI tryptase cDNA sequence matched that predicted from the published partial sequence of the mMCP-7-like I gene, and the δII tryptase cDNA matched the published exonic sequence of the mMCP-7-like II gene (Pallaoro et al., 1999). The cDNA and putative amino acid sequence of δII tryptase is shown in FIG. 2A. The cDNA sequence of δI tryptase (sequence not shown) was identical to that of δII except for two nucleotide differences; $G^{216}$ (δII cDNA) to A (δI cDNA) (nucleotide numbering starts from the translation initiation codon), and $G^{226}$ (δII cDNA) to A (δI cDNA). Of the nucleotide differences described above only the second, $G^{226}$ (δII) to A (δI), results in an altered amino acid residue in the putative protein products (Val in δII and Met in δI).

These results confirm that the primary transcript is spliced as predicted by Pallaoro et al., 1999. The consequence of this is that, compared to other tryptases, the human δ tryptases possess a premature translation termination codon ($T^{706}AA$) at the beginning of exon 6 which would result in the translation of a mature enzyme that is 40 amino acids shorter than the α/β tryptases (FIG. 3). Despite this truncation the serine protease catalytic triad $His^{44}$ $Asp^{91}$ and $Ser^{194}$ (initial Met numbered as position 1), which is an absolute requirement for proteolytic activity in these enzymes, remains intact. A further consequence of this truncation is the complete loss of the residues that comprise loop 2, one of seven that form the substrate-binding cleft in the α/β tryptases (Pereira et al., 1998; Huang et al., 1999).

A search of the dbEST database found no sequence with high similarity to any of the cDNAs cloned in the present study.

Example 2

In vivo Expression of δ Tryptase mRNA Transcripts

RT-PCR and Real-time Quantitative (RTQ) RT-PCR

Initially semi-quantitative RT-PCR (with primers F3/R3) was performed to screen a broad range of total RNA samples isolated from lung, heart, stomach, spleen, skin and colon. The expression of δ tryptase mRNA was then quantified using a real-time quantitative (RTQ) RT-PCR approach performed on a AB7700 Sequence Detection System (PE Applied Biosystems). Reverse transcription was performed using a commercial kit (Perkin Elmer). Briefly, 1 μg of total RNA purified from human lung, heart, spleen, stomach, colon, and the HMC-1 cell line were reverse transcribed according to the manufacturers instructions. In control experiments, reverse transcriptase was omitted from the reaction mixture to control for possible contamination of the sample with genomic template DNA. Total reaction volume was 50 ul.

Oligonucleotide primers (forward primer DF1=GGC CAC AGC TTT CAA ATC GT (SEQ ID NO:12), reverse primer DR1=GCA GTT AGG TGC CAT TCA CCT T) (SEQ ID NO:13) and a Taqman probe DTP1 (6FAM-CCT GCC AGG GTG ACT CCG GAG GG) (SEQ ID NO:14) were designed using the PrimerExpress software (PE Applied Biosystems) to specifically detect reverse transcribed δ tryptase mRNA, and not the mRNA of other tryptases (see FIG. 2A). Co-amplification of genomic DNA was avoided by locating the forward and reverse primers in separate exons and designing the probe so that it straddled the exon5/ exon6 boundary.

Optimal concentrations and conditions for amplification were determined using the plasmid containing the δ tryptase cDNA as template. The specificity for δ tryptase was determined by comparing PCR amplification of δ tryptase, αII tryptase, or βI tryptase cDNA templates. Cycling conditions were 50° C.-2 mins, 95° C.-10 mins, then 40-45 cycles of 95° C.-15 secs, 60° C.-60 secs.

For determination of mRNA levels, 6 μl of the appropriate RT reaction mixture was added to 12.5 μl of PCR master mix, 2.5 μl of Taqman probe (2.5 μM), 1 μl each of the forward and reverse primers (18 μM each), and 2 μl of $dH_2O$ to give a total reaction mixture of 25 μl.

Relative quantitation of δ tryptase mRNA expression in various tissues was determined by comparing the sample threshold cycle number ($C_T$), to a standard curve constructed with serial log dilutions ($10^{-1}$ ng to $10^{-8}$ ng) of a plasmid containing the δ tryptase cDNA. Relative copy number was determined using an algorithm (1 ng of plasmid=2.01342× $10^8$ copies) and then expressed per μg of total RNA.

For each RNA sample, δ tryptase expression was then normalized for β-actin expression. The relative quantity of δ tryptase mRNA was determined using commercially available Taqman probe and primers (PE Applied Biosystems), and a standard curve constructed by serial dilution of a plasmid containing the β-actin cDNA. The standard deviation for the resulting δ tryptase:β-actin ratio was determined using the equation: $CV_{ratio}=\sqrt{(CV_{\delta\ tryptase}^2+CV_{\beta\text{-}actin}^2)}$ where CV=SD/X (standard deviation/mean). Standards were tested in duplicate and samples in triplicate.

Transcript Expression in vivo

Standard RT-PCR analyses revealed that the δ tryptase genes are transcribed in a wide range of tissues. Correctly-sized ethidium bromide-staining bands were visible after 30 cycles, when amplified from RNA isolated from the HMC-1 cell line, lung, heart, stomach, spleen, skin and colon, as well as in fetal lung and heart (data not shown). Sequencing of RT-PCR products amplified from HMC-1, lung and fetal lung confirmed their identity (data not shown). The lack of contaminating sequence indicated that no other tryptase transcripts were being co-amplified.

Abundance of δ Tryptase

Figure 4:
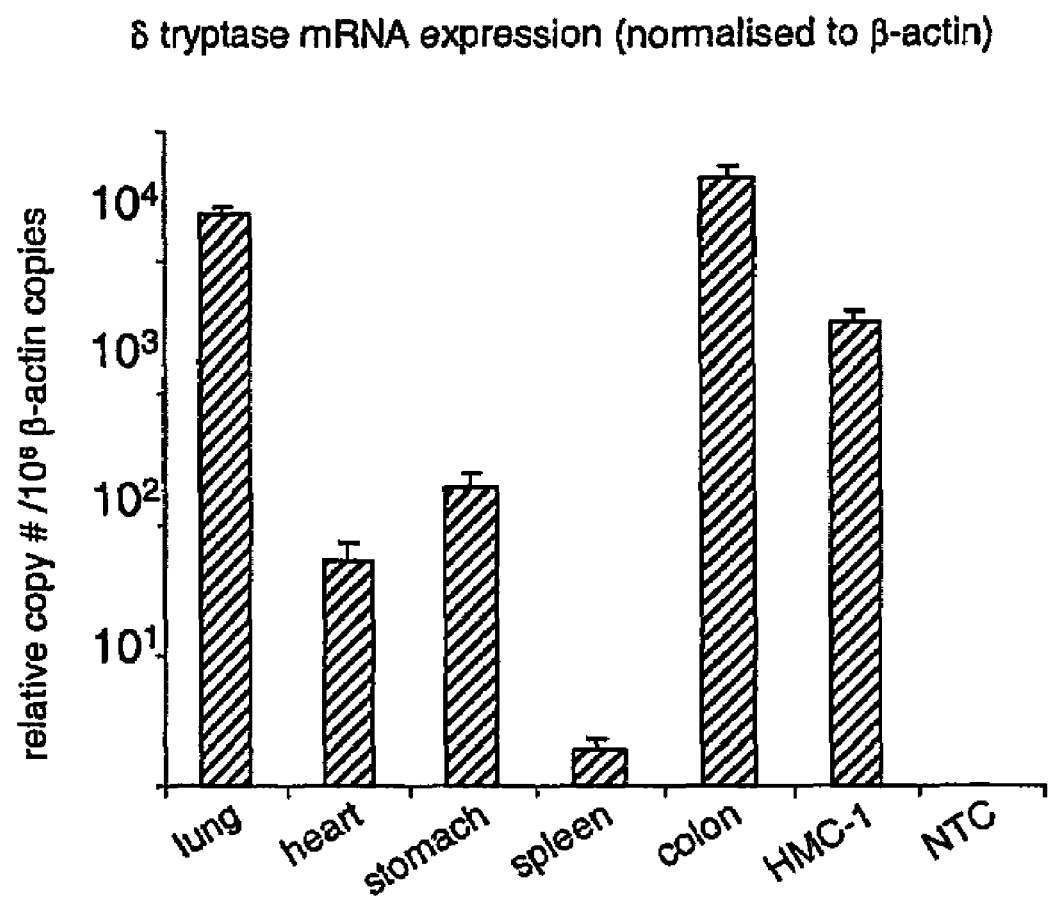
FIG. 4. δ tryptase is transcribed in various tissues. The relative abundance of δ tryptase mRNA (normalised with respect to β-actin mRNA) in a range of human tissues was determined using RTQ-RTPCR. The data represents the mean (± SD) from a single experiment. All samples were tested in triplicate and have been tested in at least two independent experiments, except for colon RNA which was tested once. NTC=no template control.

Using an RTQ-RTPCR approach, the relative abundance of δ tryptase and β-actin mRNA in a range of human tissue was determined using log-linear regressions derived from standard curves (representative regressions; δ tryptase: $y=-3.0918x+12.996$, $R^2=0.9516$, β-actin: $y=-4.0552x+11.089$, $R^2=0.9776$, where y=ng cDNA and $x=C_T$). When normalised for β-actin, δ tryptase was most abundant in the colon and lung, less abundant in the heart and stomach and just detectable in the spleen (FIG. 4). Significant amounts of δ tryptase mRNA was also detected in the HMC-1 cell line. No amplification was apparent in the no template control (NTC, FIG. 4), when primers were omitted from the PCR reaction, when other tryptase cDNAs were used as template in PCR, or when reverse transcriptase was omitted from the RT reactions (data not shown).

Example 3

Generation of an Anti-δ Tryptase Antibody

NZ white rabbits (Institute of Medical and Veterinary Science, Gilles Plains, SA, Australia) were immunised with a δ tryptase-specific peptide that possessed an amino terminal cysteine and the δ tryptase residues $Y^{162}$HTGLHTGHSFQIVRDD$^{178}$ (SEQ ID NO:15) conjugated to diphtheria toxin (Mimotopes, Melbourne Australia). The peptide sequence, located in the region translated from exon 5, has, only ~50% identify to the α/β tryptases (see FIG. 3). A search of protein databases detected no other protein that shared this epitope.

Anti-δ tryptase antibodies were affinity purified from antisera using the peptide $Y^{162}$-$D^{178}$ conjugated to thiopropyl sepharose. The specificity of the δ tryptase antibody was confirmed by western blot (see below).

Example 4

In vivo Expression of δ Tryptase Polypeptide

Western Blotting

Purified recombinant δ tryptase (~0.5 μg, see below for details) and recombinant βII tryptase (~1 μg, Promega, Madison, Wis.) were separated on a 10% SDS polyacrylamide gel and transferred to a PVDF membrane. After blocking for 2 hours at room temperature with 5% skim milk powder/TBS/ 0.1% Tween 20, membranes were incubated with affinity purified δ tryptase anti-peptide antibody (1 μg/ml in TBS/ 0.1% Tween 20). Bound primary antibody was detected using a goat anti-rabbit HRP-conjugated second antibody (Biorad, Hercules, Calif.) diluted 1/10000 (2 hrs at RT), followed by exposure to an HRP-chemiluminescence substrate for 5 mins (Renaissance Enhanced Luminol Reagent, Dupont NEN, Boston, Mass.). The resulting bands were visualised by exposure to Biomax ML photographic film (Kodak, Rochester, N.Y.). Replicate blots were probed, as described above, with normal rabbit IgG (1 μg/ml), and with the mouse monoclonal anti-tryptase antibody AA1 diluted 1/200 (Dako, Glostrup, Denmark) followed by goat anti-mouse HRP-conjugate.

Figure 5:
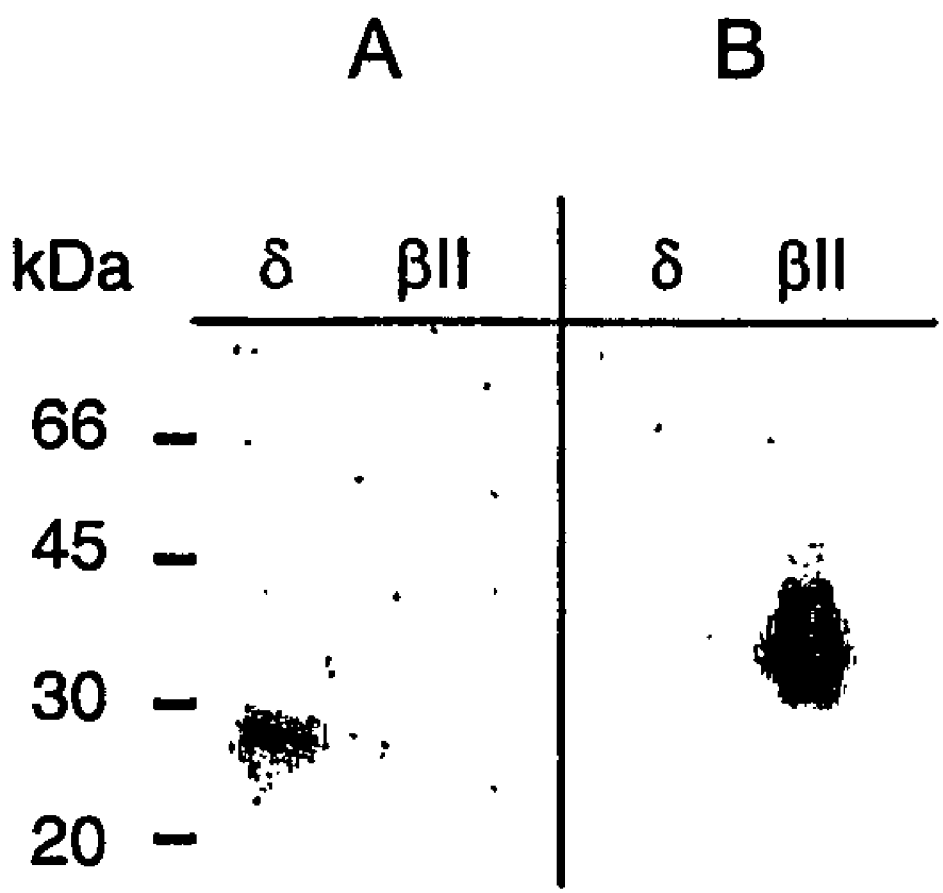
FIG. 5. Affinity purified anti-δ tryptase antibody recognises rδ tryptase but not rβII tryptase. Approximately 0.5 μg of purified rδ tryptase and 1 μg of rβII tryptase (Promega) were separated on a 10% SDS polyacrylamide gel and transferred to a PVDF membrane, blocked, and incubated with affinity purified δ tryptase anti-peptide antibody (1 μg/ml) (FIG. 5A). Replicate blots were probed with normal rabbit IgG (1 μg/ml) (data not shown), and with the mouse monoclonal anti-tryptase antibody AA1 (1/200) (FIG. 5B)

Western blot analyses indicated that the δ tryptase antibody recognised rδ tryptase (see below for details) as a single band of less than 30 kDa, but not rβII tryptase (FIG. 5A). Conversely, the AA1 antibody detected rβII tryptase as a major band of greater than 30 kDa, but did not recognise rδ tryptase (FIG. 5B).

Immunohistochemistry.

Immunohistochemistry was performed on 4 μm serial sections cut from formalin-fixed and paraffin embedded samples of human lung, colon, stomach, heart, spleen, and rheumatoid synovium. Sections were deparaffinised, dehydrated, and rinsed in tap water. Antigen retrieval was performed by incubating the sections with proteinase K (25 μg/ml in 0.1M Tris pH 7, 50 mM EDTA) at 37° C. for 30 mins. Sections were then rinsed with TBS and blocked with 20% normal goat serum/ TBS at room temperature for 20 mins. Sections were incubated with primary antibody diluted in TBS/2% BSA (δ tryptase=4 μg/ml overnight at 4° C., normal rabbit IgG=4 μg/ml overnight at 4° C., AA1 anti-tryptase antibody=1/50 dilution for 1 hour at room temperature). Sections were then washed 4 times for 5 mins in TBS, and then incubated at room temperature for 30 mins with the appropriate biotinylated secondary antibody diluted 1/200 in TBS/2% BSA: goat anti-rabbit for δ tryptase and normal rabbit IgG, and goat anti-mouse for AA1 tryptase antibody. Sections were washed 4 times for 5 mins in TBS, incubated with avidin-conjugated alkaline phosphatase (Vector Laboratories, Burlingame, Calif.) for 30 mins at RT, and then washed 4 times for 5 mins in TBS. The sections were incubated in the dark for approximately 15 mins with alkaline phosphatase substrate (Vector Red, Vector Laboratories), which gives a red reaction product in the presence of AP. All incubations were performed in a humidified chamber. Sections were rinsed in tap water, counterstained with haematoxylin for 30 seconds, rinsed in tap water and cover-slipped with CrystalMount (Biomeda, Foster City, Calif.). Stained sections were examined using an Olympus BX-60 microscope and images captured using a SPOT digital camera (Diagnostic Instruments, Sterling Heights, Mich.).

Figure 6:
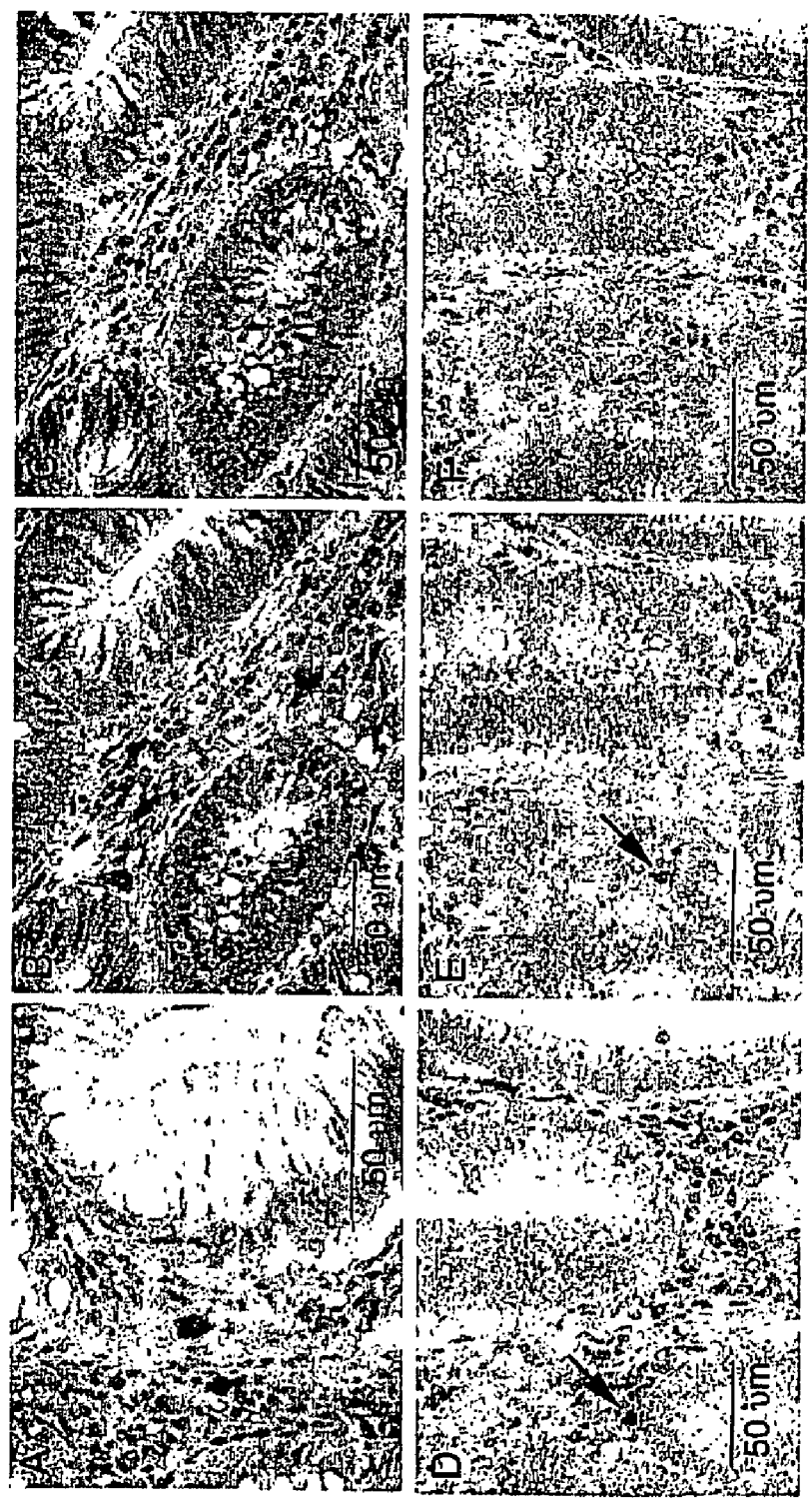
FIG. 6. δ tryptase protein is expressed in human colon tissue. Sections of human colon were stained immunohistochemically using anti-δ tryptase Ig (A,B, and E)-, the monoclonal anti-tryptase antibody AA1 (D), and normal rabbit IgG (C and F). Panels B and C, and panels D through F are serial sections. Arrows in panels D and E indicate the location of a cell that is stained with both anti-δ tryptase and the AA1 antibody.

Immunohistochemical analyses revealed that the δ tryptase polypeptide is expressed in a range of human tissue including colon (FIGS. 6A, B and E), lung, heart, and synovial tissue (data not shown). No positive-staining cells were observed in any tissue when the primary antibody was omitted, or when normal non-immune rabbit Ig was used as the primary antibody (FIGS. 6C and F). Many of the positive-staining cells possessed the morphological characteristics of mast cells. Staining of serial sections of colon tissue revealed the presence of cells that were positive for both δ tryptase (FIG. 6E) and for the α/β tryptases (ie with the AA1 antibody) (FIG. 6D) indicating that some mast cells express δ tryptase. It was noticeable in the colon tissue that the vast majority of δ tryptase-positive cells were in the mucosa, specifically in the lamina propria between the crypts δ tryptase-positive cells were virtually absent from the submucosa and muscle layers.

Example 5

Generation of Active Recombinant δ Tryptase

When compared to the α/β human tryptases, mature human δ tryptase has a 40 amino acid C-terminal truncation. To determine whether it is a functional protease, recombinant δ tryptase was expressed in bacterial cells and tested for the ability to cleave a panel of trypsin-sensitive substrates.

The recombinant fusion protein included an N terminal His-patch thioredoxin region (to increase translation efficiency and solubility), an enterokinase (EK) recognition site (to allow activation of the pro-enzyme), the mature delta tryptase sequence, and C-terminal V5 and 6×His tags (to aid detection and purification). As the δ tryptase cDNA (Genbank Accession AF206664) used to generate the expression construct did not include the sequence coding for the beginning of the mature tryptase, the forward primer (5'CAC CAT GAT TGT TGG GGG GCA GGA GGC CCC CAG GAG CAA GTG GCC CTG G 3' set forth as SEQ ID NO:16) was designed to include this region. A reverse primer (5'GGT GCC ATT CAC CTT GCA 3' set forth as SEQ ID NO:17) was designed immediately 5' of the stop codon. The resulting PCR fragment was directionally cloned into the pET102D-TOPO vector (Invitrogen), sequenced in both directions, and the construct used to transform BL21 DE3 cells. Following the addition of isopropyl-beta-thiogalactopyranoside (IPTG) (0.5 mM final concentration), the bacterial cells were incubated for 6 hours at 37° C. while being agitated vigorously. The cells were pelleted by centrifugation and resuspended in lysis buffer (50 mM NaH$_2$PO$_4$, 300 mM NaCl, 10 mM imidazole pH 8.0). The lysate was centrifuged to remove cellular debris, and the His-tagged recombinant protein purified from the supernatant using a Ni-NTA column.

To enable refolding of the protein it was first denatured in 6M Guanidine hydrochloride buffer (100 mM NaH$_2$PO$_4$, 10 mM Tris-HCl, 5 mM DTT, 6M GuHCl, pH 8.0) and introduced slowly (3 ml/hr) into refolding buffer (50 mM Tris-HCl, pH 7.5, 0.5M NaCl, 10 mM CHAPS, 2 mM DTT) while stirring gently. The refolded protein was repurified using a Ni—NTA column and dialysed with 20 mM Tris-HCl pH 7.4, 50 mM NaCl, 2 mM CaCl$_2$ overnight.

Using the same approach a recombinant form of αII tryptase was generated based on the cDNA we haves cloned (Genbank accession number AF 206665) and that matched the predicted exonic sequence of the aII gene reported by Pallaoro et al., 1999.

The recombinant enzymes were activated proteolytically by incubating the refolded purified protein with recombinant enterokinase (Novagen) for 16 hours at 20° C. in a buffer containing 20 mM Tris-HCl pH 7.4, 50 mM NaCl, 2 mM CaCl$_2$. Following activation, enterokinase was removed from the reaction mixture using an enterokinase cleavage capture kit (Novagen).

The enzymatic activity of recombinant δ tryptase was evaluated by testing its ability to cleave a panel of three trypsin-susceptible p-nitroanilide (pNA) chromogenic substrates; N-Benzoyl-Pro-Phe-Arg-pNA, D-Ile-Phe-Lys pNA, and N-p-Tosyl-Gly-Pro-Lys 4-pNA (Sigma-Adrich, St Louis, Mo.) and was compared to that of rαII tryptase, and commercially available native human lung tryptase (ICN, Costa Mesa, Calif.) and recombinant human lung βII tryptase (Promega, Madison, Wis.). Pro-δ tryptase (ie prior to removal of the EK susceptible activation peptide), recombinant EK alone, and buffer alone acted as negative controls. Approximately equal amounts (~2 μg) of the enzymes were incubated with each substrate (10 μg) at 37° C. for 2 hrs, in 100 mM HEPES pH7.5 10% glycerol (total reaction volume=50 μl), and then analysed by HPLC using a reverse-phase column (4.6×50 mM RP18 Xterra, Waters, Bedford, Mass.). In this initial investigation no exogenous heparin was added. Substrate cleavage was determined by the detection of new peaks representing the separated peptide and nitroanilide moieties. The amount of substrate cleaved was estimated by measuring the area under the HPLC peak that corresponded to the liberated peptide moiety using Delta T Scan software version 2.04 (Delta T Devices Ltd, Cambridge, UK). The retention time of the liberated nitroanilide was constant and was experimentally determined to be 2.67 mins.

Figure 7:
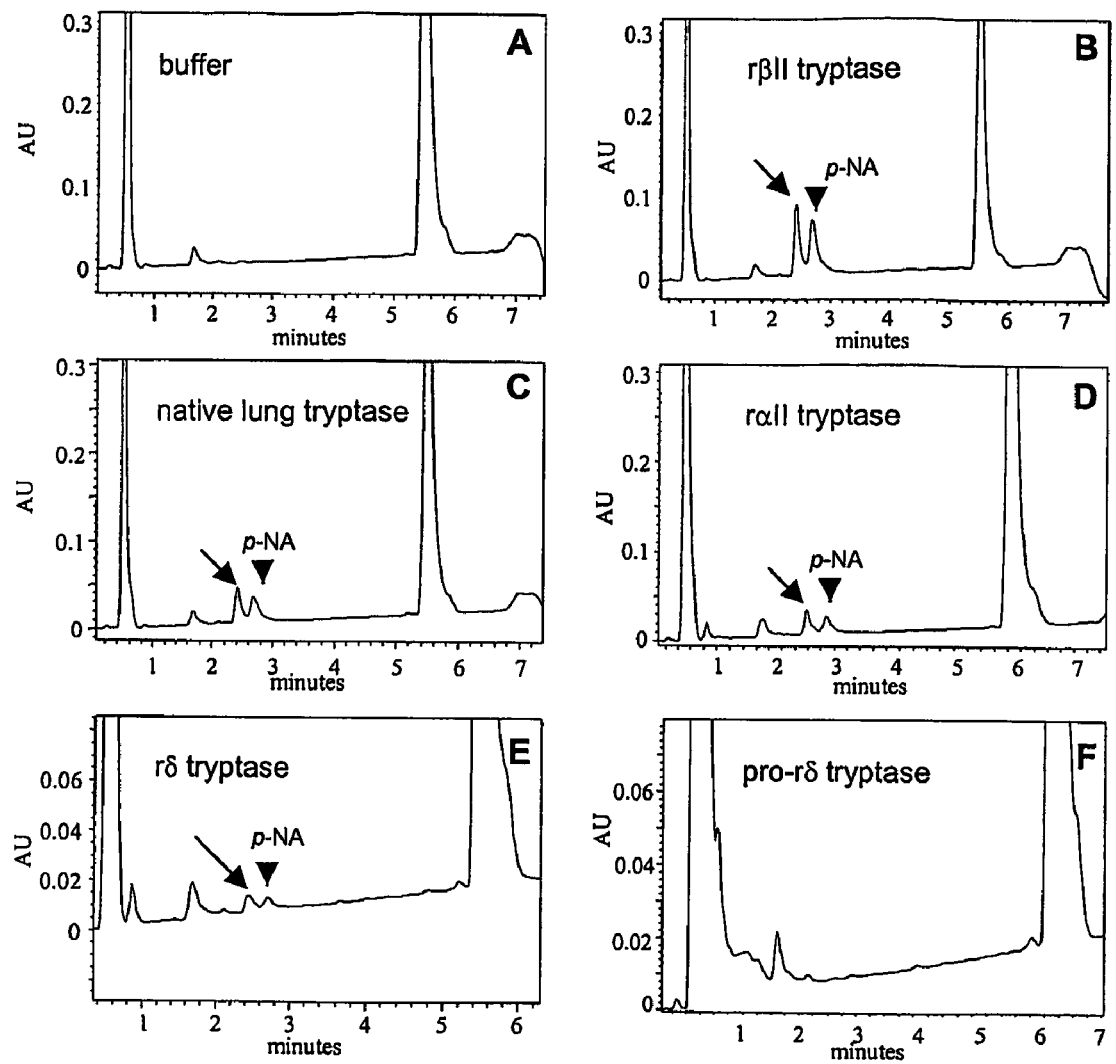
FIG. 7. rδ tryptase cleaves a trypsin-sensitive substrate. Reverse-phase HPLC of D-Ile-Phe-Lys pNA cleavage products when digested with A) buffer alone, B) rβII tryptase, C) native lung tryptase, D) rαII tryptase E) rδ tryptase, or F) pro-rδ tryptase. Approximately 2 μg of each enzyme was used to digest 10 μg of substrate in a 50 μl reaction. Liberated pNA (▼) and peptide (→) moieties are indicated. The large peak at the right of each panel (5.6 mins) represents undigested substrate. Samples were tested in duplicate and representative chromatograms are shown.

Recombinant δ tryptase was expressed in bacterial cells, purified on a metal chelating column, refolded, and the mature form of the enzyme generated by EK cleavage. The mature form of the enzyme was recognised by an anti-peptide antibody as a single band of less than 30 kDa (FIG. 5A). rδ tryptase, rαII tryptase, and commercially available rβII tryptase and native lung tryptase were tested for the ability to cleave a panel of three trypsin-susceptible pNA chromogenic substrates. rβII tryptase was able, with different efficiencies, to cleave all three substrates (FIG. 7B; N-p-Tosyl-Gly-Pro-Lys>N-Benzoyl-Pro-Phe-Arg-pNA=D-Ile-Phe-Lys pNA) (only data for D-Ile-Phe-Lys pNA is shown for all enzymes). Native lung tryptase was able to cleave two of the substrates (FIG. 7C; N-p-Tosyl-Gly-Pro-Lys>D-Ile-Phe-Lys pNA), while rαII tryptase was able to cleave all three substrates equally, but less efficiently than rβII tryptase (FIG. 7D). rδ tryptase, while ineffective against N-Benzoyl-Pro-Phe-Arg-pNA or N-p-Tosyl-Gly-Pro-Lys 4-nitroanilide, was able to cleave D-Ile-Phe-Lys pNA (FIG. 7E). No substrate cleavage was detected in the presence of buffer alone (FIG. 7A), pro-rδ tryptase (ie not activated by EK cleavage, FIG. 7F) and EK alone (data not shown). The amount of substrate cleaved by each enzyme was determined by estimating the area under the peaks that represent the liberated peptide portion of the cleaved substrate. The amount of D-Ile-Phe-Lys pNA substrate cleaved by rδ tryptase was approximately 12% as much as that cleaved by rβII tryptase.

Example 6

Cloning of a δ Tryptase Splice Variant

Source of RNA.

HMC-1 cells (5×10$^6$, a kind gift from Dr J H Butterfield) were lysed in 1 ml of TRI REAGENT™ (Sigma-Aldrich, Sydney, Australia), and 0.2 ml of chloroform added. Following centrifugation, the aqueous phase was transferred to a fresh tube and 0.5 ml of isopropanol added. The RNA pellet was collected by centrifugation, washed with 75% ethanol, dissolved in dH$_2$O and stored at −80° C. until required.

Preparation of cDNA.

First strand cDNAs were generated using the cDNA Cycle® kit (Invitrogen) from total RNA isolated from the HMC-1 cell line. 1.5 μg of HMC-1 total RNA and 1 μl of oligo (dT) primer were heated at 65° C. for 10 min to remove secondary structure. Reverse transcription was performed for 1 h at 42° C. in a solution containing 1 μl of RNase inhibitor, 4 μl of 5×RT buffer, 1 μl of 100 mM dNTPs, 1 μl of 80 mM sodium pyrophosphate and 0.5 μl AMV reverse transcriptase. The reaction was terminated by incubating the mixture at 95° C. for 2 min, and was then placed on ice immediately.

PCR Amplification and Cloning of cDNAs.

PCR amplification of first strand cDNA was performed within 2 h of the reverse transcription reaction using the primers F3=5'-TGC AGC AAA CGG GCA TTG TTG-3' (SEQ ID NO:18), and R3=5'-AAA GCT GTG GCC CGT ATG GAG-3' (SEQ ID NO:19).

The PCR reactions were carried out with 2.5 units of AmpliTaq Gold™ (Perkin Elmer, Branchburg, N.J.) and 2 µl of the reverse transcriptase reaction mixture. The total reaction volume was 50 µl with a final concentration of 10 mM Tris/HCl, pH 8.3, 50 mM KCl, 2 mM $MgCl_2$, 0.2 mM dNTPs, and 0.1 µM of the appropriate 5' and 3' primers. After an initial incubation for 5 min at 94° C., samples were subjected to 35 cycles of PCR (45 s at 95° C., 60 s at 55° C., and 60 s at 72° C.). This was followed by a final extension step of 72° C. for 10 min. PCR products (10 µl) were visualized on a 1% agarose gel. Appropriately-sized products were excised from the gel, purified with QIAquick gel extraction kit (QIAGEN, Chatsworth, Calif.) and ligated into the plasmid vector pCR-II®-TOPO (Invitrogen). The ligation mixture was then used to transform TOP10 cells (Invitrogen). The transformation mixture was plated onto LB/agar plates containing Ampicillin (50 µg/ml), and coated with X-gal to enable blue/white color selection. Plasmids containing the appropriate sized inserts were screened for the presence of tryptase cDNAs by PCR using the primer set F3/R3. Plasmid DNA was then purified from clones identified in this manner using a commercial kit (Qiagen). Nucleotide sequencing was performed either in-house using an ABI Prism® BigDye Terminator Cycle Sequencing Ready Reaction Kit and an ABI377 PRISM DNA Sequencer (PE Applied Biosystems, Foster City, Calif.), or at a core facility (SUPAMAC, Sydney, Australia).

cDNA Sequence

Sequencing revealed that the cloned cDNA was an alternately-spliced version of the delta tryptase transcript. By comparing the sequence to that of the full-length transcript and of the gene sequence, it was determined that the alternate pattern of RNA splicing results in a transcript missing the first 27 nucleotides of the region corresponding to exon 4 in the gene. Thus when translated this would result in a protein product that is 9 amino acids shorter that a protein product translated from the full-length transcript. The rest of the protein would remain unchanged as there has been no frameshift.

Example 7

Compositions for Treatment

The suitable compounds and agents identified by the methods of the present invention which are used for the treatment or prevention of disease states may be administered alone, although it is preferable that they be administered as a pharmaceutical composition.

In accordance with the best mode of performing the invention provided herein, specific preferred compositions are outlined below. The following are to be construed as merely illustrative examples of compositions and not as a limitation of the scope of the present invention in any way.

Example 7(a)

Composition for Parenteral Administration

A composition for intramuscular injection could be prepared to contain 1 mL sterile buffered water, and 1 mg of a suitable agent or compound.

Similarly, a composition for intravenous infusion may comprise 250 ml of sterile Ringer's solution, and 5 mg of a suitable agent or compound.

Example 7(b)

Injectable Parenteral Composition

A composition suitable for administration by injection may be prepared by mixing 1% by weight of a suitable agent or compound in 10% by volume propylene glycol and water. The solution is sterilised by filtration.

Example 7(c)

Capsule Composition

A composition of a suitable agent or compound in the form of a capsule may be prepared by filling a standard two-piece hard gelatin capsule with 50 mg of the agent or compound, in powdered form, 100 mg of lactose, 35 mg of talc and 10 mg of magnesium stearate.

Example 7(d)

Eye Drop Composition

A typical composition for delivery as an eye drop is outlined below:

| | |
|---|---|
| Suitable agent or compound | 0.3 g |
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The a suitable agent or compound is then added, and the solution sterilised by filtration through a membrane filter (0.22 µm pore size), and aseptically packed into sterile containers.

Example 7(e)

Composition for Inhalation Administration

For an aerosol container with a capacity of 20-30 ml: a mixture of 10 mg of a suitable agent or compound with 0.5-0.8% by weight of a lubricating agent, such as polysorbate 85 or oleic acid, is dispersed in a propellant, such as freon, and put into an appropriate aerosol container for either intranasal or oral inhalation administration.

Example 7(f)

Ointment Composition

A typical composition for delivery as an ointment includes 1.0 g of a suitable agent or compound, together with white soft paraffin to 100.0 g, dispersed to produce a smooth, homogeneous product.

Example 7(g)

Topical Cream Composition

A typical composition for delivery as a topical cream is outlined below:

| | |
|---|---|
| Suitable agent or compound | 1.0 g |
| Polawax GP 200 | 25.0 g |
| Lanolin Anhydrous | 3.0 g |
| White Beeswax | 4.5 g |
| Methyl hydroxybenzoate | 0.1 g |
| Deionised &sterilised Water to | 100.0 g |

The polawax, beeswax and lanolin are heated together at 60° C., a solution of methyl hydroxybenzoate is added and homogenisation achieved using high speed stirring. The temperature is then allowed to fall to 50° C. The agent or compound is then added and dispersed throughout, and the composition is allowed to cool with slow speed stirring.

Example 7(h)

Topical Lotion Composition

A typical composition for delivery as a topical lotion is outlined below:

| | |
|---|---|
| Suitable agent or compound | 1.2 g |
| Sorbitan Monolaurate | 0.8 g |
| Polysorbate 20 | 0.7 g |
| Cetostearyl Alcohol | 1.5 g |
| Glycerin | 7.0 g |
| Methyl Hydroxybenzoate | 0.4 g |
| Sterilised Water about to | 100.00 ml |

The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenised, allowed to cool with continuous stirring and the agent or compound is added as a suspension in the remaining water. The whole suspension is stirred until homogenised.

REFERENCES

Caughey, G. H., W. W. Raymond, J. L. Blount, W. T. H. Leola, M. Pallaoro, P. J Wolters, and G. M. Verghese. 2000. Characterization of human γ-tryptases, novel members of the chromosome 16p mast cell tryptase and prostasin gene families. *J. Immunol.* 164:6566.

Fields, S. and O. Song. 1989. A novel genetic system to detect protein-protein interactions. *Nature* 340:245.

Flanagan, J. G., and P. Leder. 1990. The kit ligand: a cell surface molecule altered in steel mutant fibroblasts. *Cell* 63:185.

Harris, J. L., A. Niles, K. Burdick, M. Maffitt, B. J. Backes, J. A. Ellman, I. Kuntz, M. Haak-Frendscho, and C. S. Craik. 2001. Definition of the extended substrate specificity determinants for β-tryptases I and II. *J. Biol. Chem.* 276:24941.

Huang, C., L. Li, S. A. Krilis, K. Chanasyk, Y. Tang, Z. Li, J. E. Hunt, and R. L. Stevens. 1999. Human tryptases α and β/II are functionally distinct, due in part to a single amino acid difference in one of the surface loops that forms the substrate binding cleft. *J. Biol. Chem.* 274:19670.

Huang C., G. Morales, A. Vagi, K. Chanasyk, M. Ferrazzi, C. Burklow, W. T. Qiu, E. Feyfant, A. Sali, and R. L. Stevens. 2000. Formation of enzymatically active, homotypic, and heterotypic tetramers of mouse mast cell tryptases. Dependence on a conserved Trp-rich domain on the surface. *J. Biol. Chem.* 275:351.

McNeil H. P., D. S. Reynolds, V. Schiller, N. Ghildyal, D. S. Gurley, K. F. Austen, and R. L. Stevens. 1992. Isolation, characterization, and transcription of the gene encoding mouse mast cell protease 7. *Proc. Natl. Acad. Sci. USA.* 89:11174.

Min, H. K., N. Kambe, and L. B. Schwartz. 2001. Human mouse mast cell protease 7-like tryptase genes are pseudogenes. *J. Allergy. Clin. Immunol.* 107:315.

Pallaoro, M., M. S. Fejzo, L. Shayesteh, J. L. Blount, and G. H. Caughey. 1999 Characterization of genes encoding known and novel human mast cell tryptases. *J. Biol. Chem.* 274:3355.

Pereira, P. J. B., B. A. Bergner, S. Macedo-Ribeiro, R. Huber, G. Matschiner, H. Fritz, C. P. Sommerhoff, and W. Bode. 1998. Human beta-tryptase is a ring-like tetramer with active sites facing a central pore. *Nature* 392:306.

Wong G W. Yasuda S. Madhusudhan M S. Li L. Yang Y. Krilis S A. Sali A. Stevens R L. 2001 Human tryptase epsilon (PRSS22), a new member of the chromosome 16p13.3 family of human serine proteases expressed in airway epithelial cells. *J. Biol. Chem.* 276(52):49169-82.

The invention claimed is:

1. A purified δ1 purified tryptase polypeptide comprising the amino acid sequence set forth in SEQ ID NO:2.

\* \* \* \* \*

SEQUENCE LISTING

```
<160> NUMBER OF SEQ ID NOS: 26

<210> SEQ ID NO 1
<211> LENGTH: 235
<212> TYPE: PRT
<213> ORGANISM: Human delta 2 tryptase

<400> SEQUENCE: 1

Met Leu Ser Leu Leu Leu Leu Ala Leu Pro Val Leu Ala Ser Pro Ala
1               5                   10                  15
```

```
Tyr Val Ala Pro Ala Pro Gly Gln Ala Leu Gln Gln Thr Gly Ile Val
            20                  25                  30

Gly Gly Gln Glu Ala Pro Arg Ser Lys Trp Pro Trp Gln Val Ser Leu
        35                  40                  45

Arg Val Arg Gly Pro Tyr Trp Met His Phe Cys Gly Gly Ser Leu Ile
    50                  55                  60

His Pro Gln Trp Val Leu Thr Ala Ala His Cys Val Glu Pro Asp Ile
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
            115                 120                 125

Glu Pro Val Asn Ile Ser Ser His Ile His Thr Val Thr Leu Pro Pro
        130                 135                 140

Ala Ser Glu Thr Phe Pro Pro Gly Met Pro Cys Trp Val Thr Gly Trp
145                 150                 155                 160

Gly Asp Val Asp Asn Asn Val His Leu Pro Pro Tyr Pro Leu Lys
                165                 170                 175

Glu Val Glu Val Pro Val Val Glu Asn His Leu Cys Asn Ala Glu Tyr
            180                 185                 190

His Thr Gly Leu His Thr Gly His Ser Phe Gln Ile Val Arg Asp Asp
                195                 200                 205

Met Leu Cys Ala Gly Ser Glu Asn His Asp Ser Cys Gln Gly Asp Ser
        210                 215                 220

Gly Gly Pro Leu Val Cys Lys Val Asn Gly Thr
225                 230                 235

<210> SEQ ID NO 2
<211> LENGTH: 235
<212> TYPE: PRT
<213> ORGANISM: Human delta 1 tryptase

<400> SEQUENCE: 2

Met Leu Ser Leu Leu Leu Ala Leu Pro Val Leu Ala Ser Pro Ala
1               5                   10                  15

Tyr Val Ala Pro Ala Pro Gly Gln Ala Leu Gln Gln Thr Gly Ile Val
            20                  25                  30

Gly Gly Gln Glu Ala Pro Arg Ser Lys Trp Pro Trp Gln Val Ser Leu
        35                  40                  45

Arg Val Arg Gly Pro Tyr Trp Met His Phe Cys Gly Gly Ser Leu Ile
    50                  55                  60

His Pro Gln Trp Val Leu Thr Ala Ala His Cys Met Glu Pro Asp Ile
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
            115                 120                 125

Glu Pro Val Asn Ile Ser Ser His Ile His Thr Val Thr Leu Pro Pro
        130                 135                 140

Ala Ser Glu Thr Phe Pro Pro Gly Met Pro Cys Trp Val Thr Gly Trp
145                 150                 155                 160
```

```
Gly Asp Val Asp Asn Asn Val His Leu Pro Pro Tyr Pro Leu Lys
                165                 170                 175

Glu Val Glu Val Pro Val Val Glu Asn His Leu Cys Asn Ala Glu Tyr
            180                 185                 190

His Thr Gly Leu His Thr Gly His Ser Phe Gln Ile Val Arg Asp Asp
        195                 200                 205

Met Leu Cys Ala Gly Ser Glu Asn His Asp Ser Cys Gln Gly Asp Ser
    210                 215                 220

Gly Gly Pro Leu Val Cys Lys Val Asn Gly Thr
225             230                 235

<210> SEQ ID NO 3
<211> LENGTH: 226
<212> TYPE: PRT
<213> ORGANISM: Human variant delta tryptase

<400> SEQUENCE: 3

Met Leu Ser Leu Leu Leu Ala Leu Pro Val Leu Ala Ser Pro Ala
1               5                   10                  15

Tyr Val Ala Pro Ala Pro Gly Gln Ala Leu Gln Thr Gly Ile Val
            20                  25                  30

Gly Gly Gln Glu Ala Pro Arg Ser Lys Trp Pro Trp Gln Val Ser Leu
        35                  40                  45

Arg Val Arg Gly Pro Tyr Trp Met His Phe Cys Gly Gly Ser Leu Ile
    50                  55                  60

His Pro Gln Trp Val Leu Thr Ala Ala His Cys Val Glu Pro Val Gln
65                  70                  75                  80

Leu Arg Glu Gln His Leu Tyr Tyr Gln Asp Gln Leu Leu Pro Val Ser
                85                  90                  95

Arg Ile Ile Val His Pro Gln Phe Tyr Ile Ile Gln Thr Gly Ala Asp
            100                 105                 110

Ile Ala Leu Leu Glu Leu Glu Glu Pro Val Asn Ile Ser Ser His Ile
        115                 120                 125

His Thr Val Thr Leu Pro Pro Ala Ser Glu Thr Phe Pro Pro Gly Met
    130                 135                 140

Pro Cys Trp Val Thr Gly Trp Gly Asp Val Asp Asn Asn Val His Leu
145                 150                 155                 160

Pro Pro Pro Tyr Pro Leu Lys Glu Val Glu Val Pro Val Val Glu Asn
                165                 170                 175

His Leu Cys Asn Ala Glu Tyr His Thr Gly Leu His Thr Gly His Ser
            180                 185                 190

Phe Gln Ile Val Arg Asp Asp Met Leu Cys Ala Gly Ser Glu Asn His
        195                 200                 205

Asp Ser Cys Gln Gly Asp Ser Gly Gly Pro Leu Val Cys Lys Val Asn
    210                 215                 220

Gly Thr
225

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
```
cccgtcctgg cgagcccg                                                18

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
cagtgaccca ggtggacac                                               19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
agtggccagg atgctgagc                                               19

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
tttggacagg aggggctggc t                                            21

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
gagcaagtgg ccctggca                                                18

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ggacatagtg gtggatccag                                              20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
tgcagcaaac gggcattgtt g                                            21

<210> SEQ ID NO 11
<211> LENGTH: 21
<212> TYPE: DNA
<213> ORGANISM: Artificial Sequence

```
<220> FEATURE:
<223> OTHER INFORMATION: Synthetic

<400> SEQUENCE: 11
aaagctgtgg cccgtatgga g                                         21

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ggccacagct ttcaaatcgt                                           20

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
gcagttaggt gccattcacc tt                                        22

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
cctgccaggg tgactccgga ggg                                       23

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Tyr His Thr Gly Leu His Thr Gly His Ser Phe Gln Ile Val Arg Asp
1               5                   10                  15

Asp

<210> SEQ ID NO 16
<211> LENGTH: 49
<212> TYPE: DNA
<213> ORGANISM: Artificial Sequence
<220> FEATURE:
<223> OTHER INFORMATION: Synthetic

<400> SEQUENCE: 16
caccatgatt gttgggggc aggaggcccc caggagcaag tggccctgg             49

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
```

```
ggtgccattc accttgca                                                      18

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
tgcagcaaac gggcattgtt g                                                  21

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
aaagctgtgg cccgtatgga g                                                  21

<210> SEQ ID NO 20
<211> LENGTH: 810
<212> TYPE: DNA
<213> ORGANISM: Human delta 2 tryptase

<400> SEQUENCE: 20
atgctgagcc tgctgctgct ggcgctgccc gtcctggcga gcccggccta cgtggcccct        60
gccccaggcc aggccctgca gcaaacgggc attgttgggg gcaggaggc ccccaggagc        120 aagtggccct gcaggtgag cctgagagtc cgcggcccat actggatgca cttctgcggg        180
ggctccctca tccacccca gtgggtgcta accgcggcgc actgcgtgga accggacatc        240
aaggatctgg ccgccctcag ggtgcaactg cgggagcagc acctctacta ccaggaccag        300
ctgctgccgg tcagcaggat catcgtgcac ccacagttct acatcatcca gaccggggcg        360
gacatcgccc tgctggagct ggaggagccc gtgaacatct ccagccacat ccacacggtc        420
acgctgcccc ctgcctcgga gccttcccc ccggggatgc cgtgctgggt cactggctgg        480
ggcgacgtgg acaataatgt gcacctgccg ccgccatacc cgctgaagga ggtgaagtc        540 cccgtagtgg aaaaccacct ttgcaacgcg gaatatcaca ccggcctcca tacgggccac        600
agctttcaaa tcgtccgcga tgacatgctg tgtgcgggga cgaaaatca cgactcctgc        660 cagggtgact ctggagggcc cctggtctgc aaggtgaatg gcacctaact gcaggcgggc        720
gtggtcagct gggaggagag ctgtgcccag cccaaccggc ctggcatcta cacccgtgtc        780
acctactact ggactggat ccaccactat                                          810

<210> SEQ ID NO 21
<211> LENGTH: 194
<212> TYPE: PRT
<213> ORGANISM: Human variant delta tryptase

<400> SEQUENCE: 21

Gly Gly Gln Glu Ala Pro Arg Ser Lys Trp Pro Trp Gln Val Ser Leu
1               5                   10                  15

Arg Val Arg Gly Pro Tyr Trp Met His Phe Cys Gly Gly Ser Leu Ile
            20                  25                  30

His Pro Gln Trp Val Leu Thr Ala Ala His Cys Val Glu Pro Val Gln
        35                  40                  45
```

```
Leu Arg Glu Gln His Leu Tyr Tyr Gln Asp Gln Leu Pro Val Ser
     50                  55                  60

Arg Ile Ile Val His Pro Gln Phe Tyr Ile Ile Gln Thr Gly Ala Asp
 65                  70                  75                  80

Ile Ala Leu Leu Glu Leu Glu Pro Val Asn Ile Ser Ser His Ile
                 85                  90                  95

His Thr Val Thr Leu Pro Pro Ala Ser Glu Thr Phe Pro Pro Gly Met
                100                 105                 110

Pro Cys Trp Val Thr Gly Trp Gly Asp Val Asp Asn Asn Val His Leu
                115                 120                 125

Pro Pro Pro Tyr Pro Leu Lys Glu Val Glu Val Pro Val Val Glu Asn
            130                 135                 140

His Leu Cys Asn Ala Glu Tyr His Thr Gly Leu His Thr Gly His Ser
145                 150                 155                 160

Phe Gln Ile Val Arg Asp Asp Met Leu Cys Ala Gly Ser Glu Asn His
                165                 170                 175

Asp Ser Cys Gln Gly Asp Ser Gly Gly Pro Leu Val Cys Lys Val Asn
                180                 185                 190

Gly Thr

<210> SEQ ID NO 22
<211> LENGTH: 275
<212> TYPE: PRT
<213> ORGANISM: Human alpha 1 tryptase

<400> SEQUENCE: 22

Met Leu Ser Leu Leu Leu Ala Leu Pro Val Leu Ala Ser Arg Ala
 1               5                  10                  15

Tyr Ala Ala Pro Ala Pro Val Gln Ala Leu Gln Gln Ala Gly Ile Val
                 20                  25                  30

Gly Gly Gln Glu Ala Pro Arg Ser Lys Trp Pro Trp Gln Val Ser Leu
             35                  40                  45

Arg Val Arg Asp Arg Tyr Trp Met His Phe Cys Gly Gly Ser Leu Ile
 50                  55                  60

His Pro Gln Trp Val Leu Thr Ala Ala His Cys Leu Gly Pro Asp Val
 65                  70                  75                  80

Lys Asp Leu Ala Thr Leu Arg Val Gln Leu Arg Glu Gln His Leu Tyr
                 85                  90                  95

Tyr Gln Asp Gln Leu Leu Pro Val Ser Arg Ile Ile Val His Pro Gln
                100                 105                 110

Phe Tyr Ile Ile Gln Thr Gly Ala Asp Ile Ala Leu Leu Glu Leu Glu
            115                 120                 125

Glu Pro Val Asn Ile Ser Ser Arg Val His Thr Val Met Leu Pro Pro
130                 135                 140

Ala Ser Glu Thr Phe Pro Pro Gly Met Pro Cys Trp Val Thr Gly Trp
145                 150                 155                 160

Gly Asp Val Asp Asn Asp Glu Pro Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
        195                 200                 205

Met Leu Cys Ala Gly Asn Ser Gln Arg Asp Ser Cys Lys Gly Asp Ser
210                 215                 220
```

```
Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
            245                 250                 255

Tyr Thr Arg Val Thr Tyr Tyr Leu Asp Trp Ile His His Tyr Val Pro
        260                 265                 270

Lys Lys Pro
        275

<210> SEQ ID NO 23
<211> LENGTH: 275
<212> TYPE: PRT
<213> ORGANISM: Human alpha 2 tryptase

<400> SEQUENCE: 23

Met Leu Ser Leu Leu Leu Ala Leu Pro Val Leu Ala Ser Pro Ala
1               5                   10                  15

Tyr Ala Ala Pro Ala Pro Val Gln Ala Leu Gln Gln Ala Gly Ile Val
                20                  25                  30

Gly Gly Gln Glu Ala Pro Arg Ser Lys Trp Pro Trp Gln Val Ser Leu
            35                  40                  45

Arg Val Arg Asp Arg Tyr Trp Met His Phe Cys Gly Gly Ser Leu Ile
50                  55                  60

His Pro Gln Trp Val Leu Thr Ala Ala His Cys Leu Gly Pro Asp Val
65                  70                  75                  80

Lys Asp Leu Ala Thr Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
        115                 120                 125

Glu Pro Val Asn Ile Ser Ser Arg Val His Thr Val Met Leu Pro Pro
130                 135                 140

Ala Ser Glu Thr Phe Pro Pro Gly Met Pro Cys Trp Val Thr Gly Trp
145                 150                 155                 160

Gly Asp Val Asp Asn Asp Glu Pro Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
        195                 200                 205

Met Leu Cys Ala Gly Asn Thr Arg Arg Asp Ser Cys Gln Gly Asp Ser
210                 215                 220

Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
            245                 250                 255

Tyr Thr Arg Val Thr Tyr Tyr Leu Asp Trp Ile His His Tyr Val Pro
        260                 265                 270

Lys Lys Pro
        275

<210> SEQ ID NO 24
<211> LENGTH: 275
<212> TYPE: PRT
```

-continued

<213> ORGANISM: Human beta 1 tryptase

<400> SEQUENCE: 24

Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
                20                  25                  30

Gly Gly Gln Glu Ala Pro Arg Ser Lys Trp Pro Trp Gln Val Ser Leu
            35                  40                  45

Arg Val His Gly Pro Tyr Trp Met His Phe Cys Gly Gly Ser Leu Ile
        50                  55                  60

His Pro Gln Trp Val Leu Thr Ala Ala His Cys Val Gly Pro Asp Val
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Thr Ala Gln Ile Gly Ala Asp Ile Ala Leu Leu Glu Leu Glu
        115                 120                 125

Glu Pro Val Asn Val Ser Ser His Val His Thr Val Thr Leu Pro Pro
130                 135                 140

Ala Ser Glu Thr Phe Pro Pro Gly Met Pro Cys Trp Val Thr Gly Trp
145                 150                 155                 160

Gly Asp Val Asp Asn Asp Glu Arg Leu Pro Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Val Arg Asp Asp
        195                 200                 205

Met Leu Cys Ala Gly Asn Thr Arg Arg Asp Ser Cys Gln Gly Asp Ser
210                 215                 220

Gly Gly Pro Leu Val Cys Lys Val Asn Gly Thr Trp Leu Gln Ala Gly
225                 230                 235                 240

Val Val Ser Trp Gly Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
            260                 265                 270

Lys Lys Pro
        275

<210> SEQ ID NO 25
<211> LENGTH: 275
<212> TYPE: PRT
<213> ORGANISM: Human beta 2 tryptase

<400> SEQUENCE: 25

Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
                20                  25                  30

Gly Gly Gln Glu Ala Pro Arg Ser Lys Trp Pro Trp Gln Val Ser Leu
            35                  40                  45

Arg Val His Gly Pro Tyr Trp Met His Phe Cys Gly Gly Ser Leu Ile
        50                  55                  60

His Pro Gln Trp Val Leu Thr Ala Ala His Cys Val Gly Pro Asp Val

-continued

```
                65                  70                  75                  80
Lys Asp Leu Ala Ala Leu Arg Val Gln Leu Arg Glu Gln His Leu Tyr
                    85                  90                  95

Tyr Gln Asp Gln Leu Leu Pro Val Ser Arg Ile Ile Val His Pro Gln
                100                 105                 110

Phe Tyr Thr Ala Gln Ile Gly Ala Asp Ile Ala Leu Leu Glu Leu Glu
                115                 120                 125

Glu Pro Val Lys Val Ser Ser His Val His Thr Val Thr Leu Pro Pro
            130                 135                 140

Ala Ser Glu Thr Phe Pro Pro Gly Met Pro Cys Trp Val Thr Gly Trp
145                 150                 155                 160

Gly Asp Val Asp Asn Asp Glu Arg Leu Pro Pro Pro Phe Pro Leu Lys
                165                 170                 175

Gln Val Lys Val Pro Ile Met Glu Asn His Ile Cys Asp Ala Lys Tyr
                180                 185                 190

His Leu Gly Ala Tyr Thr Gly Asp Asp Val Arg Ile Val Arg Asp Asp
                195                 200                 205

Met Leu Cys Ala Gly Asn Thr Arg Arg Asp Ser Cys Gln Gly Asp Ser
    210                 215                 220

Gly Gly Pro Leu Val Cys Lys Val Asn Gly Thr Trp Leu Gln Ala Gly
225                 230                 235                 240

Val Val Ser Trp Gly Glu Gly Cys Ala Gln Pro Asn Arg Pro Gly Ile
                    245                 250                 255

Tyr Thr Arg Val Thr Tyr Tyr Leu Asp Trp Ile His His Tyr Val Pro
                260                 265                 270

Lys Lys Pro
        275

<210> SEQ ID NO 26
<211> LENGTH: 275
<212> TYPE: PRT
<213> ORGANISM: Human beta 3 tryptase

<400> SEQUENCE: 26

Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
                    20                  25                  30

Gly Gly Gln Glu Ala Pro Arg Ser Lys Trp Pro Trp Gln Val Ser Leu
                35                  40                  45

Arg Val Arg Asp Arg Tyr Trp Met His Phe Cys Gly Gly Ser Leu Ile
            50                  55                  60

His Pro Gln Trp Val Leu Thr Ala Ala His Cys Val Gly Pro Asp Val
65                  70                  75                  80

Lys Asp Leu Ala Ala Leu Arg Val Gln Leu Arg Glu Gln His Leu Tyr
                    85                  90                  95

Tyr Gln Asp Gln Leu Leu Pro Val Ser Arg Ile Ile Val His Pro Gln
                100                 105                 110

Phe Tyr Thr Ala Gln Ile Gly Ala Asp Ile Ala Leu Leu Glu Leu Glu
                115                 120                 125

Glu Pro Val Asn Ile Ser Ser Arg Val His Thr Val Met Leu Pro Pro
            130                 135                 140

Ala Ser Glu Thr Phe Pro Pro Gly Met Pro Cys Trp Val Thr Gly Trp
145                 150                 155                 160
```

-continued

```
Gly Asp Val Asp Asn Asp Glu Arg Leu Pro Pro Phe Pro Leu Lys
            165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Val Arg Asp Asp
            195                 200                 205

Met Leu Cys Ala Gly Asn Thr Arg Arg Asp Ser Cys Gln Gly Asp Ser
    210                 215                 220

Gly Gly Pro Leu Val Cys Lys Val Asn Gly Thr Trp Leu Gln Ala Gly
225                 230                 235                 240

Val Val Ser Trp Gly Glu Gly Cys Ala Gln Pro Asn Arg Pro Gly Ile
            245                 250                 255

Tyr Thr Arg Val Thr Tyr Tyr Leu Asp Trp Ile His His Tyr Val Pro
            260                 265                 270

Lys Lys Pro
        275
```